US012564437B2

(12) United States Patent
Germain et al.

(10) Patent No.: US 12,564,437 B2
(45) Date of Patent: Mar. 3, 2026

(54) MEDICAL DEVICE AND METHODS

(71) Applicant: MINERVA SURGICAL, INC., Santa Clara, CA (US)

(72) Inventors: Aaron Germain, Campbell, CA (US); Csaba Truckai, Saratoga, CA (US)

(73) Assignee: MINERVA SURGICAL, INC., Santa Clara, CA (US)

( * ) Notice: Subject to any disclaimer, the term of this patent is extended or adjusted under 35 U.S.C. 154(b) by 169 days.

(21) Appl. No.: 18/603,934

(22) Filed: Mar. 13, 2024

(65) Prior Publication Data

US 2024/0206958 A1 Jun. 27, 2024

Related U.S. Application Data

(63) Continuation of application No. 17/744,321, filed on May 13, 2022, now Pat. No. 11,957,407, which is a
(Continued)

(51) Int. Cl.
*A61B 18/14* (2006.01)
*A61B 1/015* (2006.01)
(Continued)

(52) U.S. Cl.
CPC .......... *A61B 18/1485* (2013.01); *A61B 1/015* (2013.01); *A61B 1/018* (2013.01);
(Continued)

(58) Field of Classification Search
CPC ... A61B 18/1485; A61B 18/042; A61B 1/015; A61B 1/018; A61B 1/303; A61B 17/32002
See application file for complete search history.

(56) References Cited

U.S. PATENT DOCUMENTS

| | | | |
|---|---|---|---|
| 3,850,162 A | 11/1974 | Iglesias | |
| 3,877,433 A | 4/1975 | Librach | |

(Continued)

FOREIGN PATENT DOCUMENTS

| | | |
|---|---|---|
| EP | 0153190 A1 | 8/1985 |
| EP | 2100567 A1 | 9/2009 |

(Continued)

OTHER PUBLICATIONS

International Search Report and Written Opinion dated Sep. 24, 2012 for International Application No. PCT/US2012/043892.
(Continued)

*Primary Examiner* — Tuan V Nguyen

(74) *Attorney, Agent, or Firm* — Seager, Tufte & Wickhem, LLP

(57) ABSTRACT

Hysteroscopic system includes a hysteroscope having a main body coupled to an extension portion. The extension portion may be a shaft configured to extend transcervically to a patient's uterine cavity. First, second, and third channels extend from the main body to a distal end of the extension portion. A fluid source is coupleable to a proximal end of the first channel, and a pressure sensor is coupleable to a proximal end of the second channel. A tissue resecting probe is configured for introduction through the third channel. At least one resistance feature is included which is configured to provide a selected level of resistance to axial sliding of the probe through the third channel while permitting rotation of the probe within the third channel.

20 Claims, 23 Drawing Sheets

Related U.S. Application Data continuation of application No. 16/717,354, filed on Dec. 17, 2019, now Pat. No. 11,350,985, which is a continuation of application No. 15/240,546, filed on Aug. 18, 2016, now Pat. No. 10,531,912, which is a continuation of application No. 13/745,439, filed on Jan. 18, 2013, now Pat. No. 9,439,677.

(60) Provisional application No. 61/659,312, filed on Jun. 13, 2012, provisional application No. 61/635,803, filed on Apr. 19, 2012, provisional application No. 61/589,168, filed on Jan. 20, 2012.

(51) Int. Cl.

| | |
|---|---|
| *A61B 1/018* | (2006.01) |
| *A61B 1/303* | (2006.01) |
| *A61B 17/3207* | (2006.01) |
| *A61B 17/42* | (2006.01) |
| *A61B 18/00* | (2006.01) |
| *A61B 18/04* | (2006.01) |

(52) U.S. Cl.
CPC .............. *A61B 1/303* (2013.01); *A61B 17/42* (2013.01); *A61B 18/042* (2013.01); *A61B 17/320783* (2013.01); *A61B 2017/4216* (2013.01); *A61B 2018/00196* (2013.01); *A61B 2018/00559* (2013.01); *A61B 2018/00577* (2013.01); *A61B 2018/00601* (2013.01)

(56) References Cited

U.S. PATENT DOCUMENTS

| | | |
|---|---|---|
| 3,945,375 A | 3/1976 | Banko |
| 4,203,444 A | 5/1980 | Bonnell et al. |
| 4,369,768 A | 1/1983 | Vukovic |
| 4,400,168 A | 8/1983 | Buechel et al. |
| 4,606,330 A | 8/1986 | Bonnet |
| 4,700,694 A | 10/1987 | Shishido |
| 4,735,603 A | 4/1988 | Goodson |
| 4,955,882 A | 9/1990 | Hakky |
| 4,998,527 A | 3/1991 | Meyer |
| 5,009,656 A | 4/1991 | Reimels |
| 5,098,375 A | 3/1992 | Baier |
| 5,106,364 A | 4/1992 | Hayafuji et al. |
| 5,169,397 A | 12/1992 | Sakashita et al. |
| 5,195,541 A | 3/1993 | Obenchain |
| 5,217,466 A | 6/1993 | Hasson |
| 5,217,479 A | 6/1993 | Shuler |
| 5,277,696 A | 1/1994 | Hagen |
| 5,312,399 A | 5/1994 | Hakky et al. |
| 5,320,091 A | 6/1994 | Grossi et al. |
| 5,382,229 A | 1/1995 | Grabenkort et al. |
| 5,456,689 A | 10/1995 | Kresch et al. |
| 5,483,951 A | 1/1996 | Frassica et al. |
| 5,514,091 A | 5/1996 | Yoon |
| 5,527,331 A | 6/1996 | Kresch et al. |
| 5,536,234 A | 7/1996 | Newman |
| 5,697,281 A | 12/1997 | Eggers et al. |
| 5,730,752 A | 3/1998 | Alden et al. |
| 5,749,889 A | 5/1998 | Bacich et al. |
| 5,759,185 A | 6/1998 | Grinberg |
| 5,810,776 A | 9/1998 | Bacich et al. |
| 5,810,876 A | 9/1998 | Kelleher |
| 5,823,971 A | 10/1998 | Robinson et al. |
| 5,823,990 A | 10/1998 | Henley |
| 5,830,180 A | 11/1998 | Chandler et al. |
| 5,873,886 A | 2/1999 | Larsen et al. |
| 5,885,277 A | 3/1999 | Korth |
| 5,902,264 A | 5/1999 | Toso et al. |
| 5,906,615 A | 5/1999 | Thompson |
| 5,941,876 A | 8/1999 | Nardella et al. |
| 5,997,534 A | 12/1999 | Tu et al. |
| 6,004,319 A | 12/1999 | Goble et al. |
| 6,024,751 A | 2/2000 | Lovato et al. |
| 6,032,673 A | 3/2000 | Savage et al. |
| 6,056,746 A | 5/2000 | Goble et al. |
| 6,090,106 A | 7/2000 | Goble et al. |
| 6,113,594 A | 9/2000 | Savage |
| RE36,914 E | 10/2000 | Carlsen et al. |
| 6,149,620 A | 11/2000 | Baker et al. |
| 6,159,160 A | 12/2000 | Hsei et al. |
| 6,206,014 B1 | 3/2001 | Cameron, III et al. |
| 6,245,084 B1 | 6/2001 | Mark et al. |
| 6,293,942 B1 | 9/2001 | Goble et al. |
| 6,358,263 B2 | 3/2002 | Mark et al. |
| 6,629,986 B1 | 10/2003 | Ross et al. |
| 6,832,996 B2 | 12/2004 | Woloszko et al. |
| 6,979,332 B2 | 12/2005 | Adams |
| 7,029,451 B2 | 4/2006 | Anderson et al. |
| 7,070,604 B1 | 7/2006 | Garito et al. |
| 7,204,821 B1 | 4/2007 | Clare et al. |
| 7,226,459 B2 | 6/2007 | Cesarini et al. |
| 7,244,256 B2 | 7/2007 | DeCesare et al. |
| 7,249,602 B1 | 7/2007 | Emanuel |
| 7,384,417 B2 | 6/2008 | Cucin |
| 7,678,070 B2 | 3/2010 | Kumar et al. |
| 7,901,403 B2 | 3/2011 | Woloszko et al. |
| 7,918,822 B2 | 4/2011 | Kumar et al. |
| 8,061,359 B2 | 11/2011 | Emanuel |
| 8,123,750 B2 | 2/2012 | Norton et al. |
| 8,226,549 B2 | 7/2012 | Kumar et al. |
| 8,267,934 B2 | 9/2012 | Earley et al. |
| 8,308,726 B2 | 11/2012 | Kumar et al. |
| 8,388,570 B2 | 3/2013 | Kumar et al. |
| 8,460,178 B2 | 6/2013 | Kumar et al. |
| 8,512,283 B2 | 8/2013 | Kumar et al. |
| 8,512,326 B2 | 8/2013 | Shadduck et al. |
| 8,568,424 B2 | 10/2013 | Shugrue et al. |
| 8,574,253 B2 | 11/2013 | Gruber et al. |
| 8,591,464 B2 | 11/2013 | Kumar et al. |
| 8,652,089 B2 | 2/2014 | Kumar et al. |
| 8,663,216 B2 | 3/2014 | Davison et al. |
| 8,840,625 B2 | 9/2014 | Adams et al. |
| 8,840,626 B2 | 9/2014 | Adams et al. |
| 8,893,722 B2 | 11/2014 | Emanuel |
| 8,951,274 B2 | 2/2015 | Adams et al. |
| 8,974,448 B2 | 3/2015 | Germain et al. |
| 9,084,847 B2 | 7/2015 | Klein et al. |
| 9,233,193 B2 | 1/2016 | Truckai et al. |
| 9,254,142 B2 | 2/2016 | Germain et al. |
| 9,439,720 B2 | 9/2016 | Germain et al. |
| 9,597,149 B2 | 3/2017 | Germain et al. |
| 9,737,362 B2 | 8/2017 | Germain et al. |
| 2001/0018550 A1 | 8/2001 | Boebel et al. |
| 2001/0018559 A1 | 8/2001 | Itgaki et al. |
| 2003/0050639 A1* | 3/2003 | Yachia ............ A61B 17/32002 606/49 |
| 2003/0060862 A1 | 3/2003 | Goble et al. |
| 2003/0125607 A1* | 7/2003 | Boebel ............... A61B 1/00163 600/130 |
| 2004/0049217 A1 | 3/2004 | Ross et al. |
| 2004/0167427 A1 | 8/2004 | Quick et al. |
| 2004/0167428 A1 | 8/2004 | Quick et al. |
| 2004/0230190 A1 | 11/2004 | Dahla et al. |
| 2005/0096649 A1 | 5/2005 | Adams |
| 2005/0119529 A1 | 6/2005 | Farr et al. |
| 2005/0272975 A1 | 12/2005 | McWeeney et al. |
| 2006/0047185 A1 | 3/2006 | Shener et al. |
| 2006/0047240 A1 | 3/2006 | Kumar et al. |
| 2006/0122556 A1 | 6/2006 | Kumar |
| 2006/0122557 A1 | 6/2006 | Kumar et al. |
| 2006/0253128 A1 | 11/2006 | Sekine et al. |
| 2007/0021713 A1 | 1/2007 | Kumar et al. |
| 2007/0073098 A1 | 3/2007 | Lenker et al. |
| 2008/0021447 A1 | 1/2008 | Davison et al. |
| 2008/0051708 A1 | 2/2008 | Kumar et al. |
| 2008/0058588 A1 | 3/2008 | Emanuel |
| 2008/0058842 A1 | 3/2008 | Emanuel |
| 2008/0065060 A1 | 3/2008 | Ein-Gal |
| 2008/0071269 A1 | 3/2008 | Hilario et al. |
| 2008/0091061 A1 | 4/2008 | Kumar et al. |
| 2008/0091071 A1 | 4/2008 | Kumar et al. |

(56)                    References Cited

U.S. PATENT DOCUMENTS

| | | |
|---|---|---|
| 2008/0091074 A1 | 4/2008 | Kumar et al. |
| 2008/0097468 A1 | 4/2008 | Adams et al. |
| 2008/0097471 A1 | 4/2008 | Adams et al. |
| 2008/0249366 A1 | 10/2008 | Gruber et al. |
| 2008/0249553 A1 | 10/2008 | Gruber et al. |
| 2008/0287893 A1 | 11/2008 | Ineson |
| 2009/0137943 A1 | 5/2009 | Stearns et al. |
| 2009/0270812 A1 | 10/2009 | Litscher et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0100091 A1 | 4/2010 | Truckai |
| 2011/0213300 A1 | 9/2011 | McWeeney et al. |
| 2011/0224486 A1 | 9/2011 | Nguyen et al. |
| 2012/0010464 A1 | 1/2012 | Adams et al. |
| 2012/0172888 A1 | 7/2012 | Shugrue et al. |
| 2012/0172889 A1 | 7/2012 | Chin et al. |
| 2012/0197280 A1 | 8/2012 | Emanuel |
| 2012/0271110 A1 | 10/2012 | Kumar et al. |
| 2013/0046316 A1 | 2/2013 | Sullivan et al. |
| 2014/0074136 A1 | 3/2014 | Emanuel |
| 2015/0012023 A1 | 1/2015 | Emanuel |

FOREIGN PATENT DOCUMENTS

| | | | |
|---|---|---|---|
| GB | 2327351 A | 1/1999 | |
| JP | 55000199 A | 1/1980 | |
| JP | 1986185240 A | 8/1986 | |
| JP | 1989087708 U | 6/1989 | |
| JP | 06225851 A | 8/1994 | |
| JP | 1993293114 A | 6/1996 | |
| JP | 61185240 A | 8/1996 | |
| JP | 09084756 A | 3/1997 | |
| JP | 2002529185 A | 9/2002 | |
| JP | 2005529674 A | 10/2005 | |
| JP | 2008511397 A | 4/2008 | |
| JP | 2011212450 A | 10/2011 | |
| WO | 2010096139 A2 | 8/2010 | |
| WO | 2010127174 A1 | 11/2010 | |
| WO | 2010096139 A3 | 12/2011 | |
| WO | 20130442243 A1 | 3/2013 | |

OTHER PUBLICATIONS

International Search Report and Written Opinion dated Oct. 2, 2012 for International Application No. PCT/US2012/045428.

International Search Report and Written Opinion dated Dec. 4, 2012 for International Application No. PCT/US2012/056936.

International Search Report and Written Opinion dated May 15, 2013 for International Application No. PCT/US2013/022559.

International Search Report and Written Opinion dated Oct. 16, 2012 for International Application No. PCT/US2012/044609.

* cited by examiner

FLUID MANAGEMENT
SYSTEM 126

FLUID CONTAINER 128

FLUID SOURCE 120

PUMP 130

NEG. PRESSURE SOURCE 125

TISSUE CUTTING DEVICE 100

HYSTEROSCOPE 50

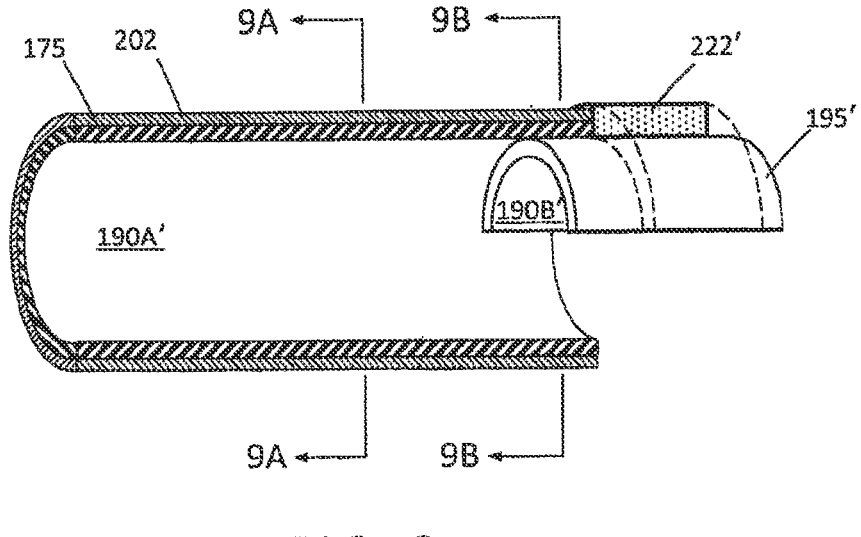
FIG. 8
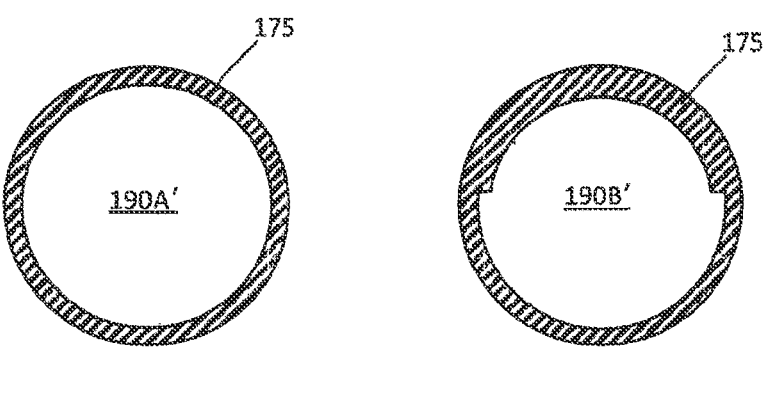
FIG. 9A                    FIG. 9B

CONTROLLER 545

MEDICAL DEVICE AND METHODS

CROSS-REFERENCE TO RELATED APPLICATIONS

This application is a continuation of U.S. application Ser. No. 17/744,321, filed May 13, 2022; which is a continuation of U.S. application Ser. No. 16/717,354, filed Dec. 17, 2019, now U.S. Pat. No. 11,350,985; which is a continuation of U.S. application Ser. No. 15/240,546, filed Aug. 18, 2016, now U.S. Pat. No. 10,531,912; which is a continuation of U.S. application Ser. No. 13/745,439, filed Jan. 18, 2013, now U.S. Pat. No. 9,439,677; which application claims the benefit of U.S. Provisional Application No. 61/589,168, filed Jan. 20, 2012; U.S. Provisional Application No. 61/635,803, filed Apr. 19, 2012; and U.S. Provisional Application No. 61/659,312, filed Jun. 13, 2012; the full disclosures of which are incorporated herein by reference.

TECHNICAL FIELD

The present invention relates to systems and methods for the resection and extraction of uterine fibroid tissue, polyps and other abnormal uterine tissue.

BACKGROUND

Uterine fibroids are non-cancerous tumors that develop in the wall of uterus. Such fibroids occur in a large percentage of the female population, with some studies indicating that up to 40 percent of all women have fibroids. Uterine fibroids can grow over time to be several centimeters in diameter and symptoms can include menorrhagia, reproductive dysfunction, pelvic pressure and pain.

One current treatment of fibroids is hysteroscopic resection or myomectomy which involves transcervical access to the uterus with a hysteroscope together with insertion of a cutting instrument through a working channel in the hysteroscope. The cutting instrument may be a mechanical tissue cutter or an electrosurgical resection device such as a cutting loop. Mechanical cutting devices are disclosed in U.S. Pat. Nos. 7,226,459; 6,032,673 and 5,730,752 and U.S. Published Patent Appl. No. 2009/0270898. An electrosurgical resecting device is disclosed in U.S. Pat. No. 5,906,615.

While hysteroscopic resection can be effective in removing uterine fibroids and polyps, one difficulty that may be encountered with resecting instruments is control of the instrument in the working channel of the hysteroscope. Typically, the resecting instrument is free to both rotate and axially translate within the working channel. While rotation of the instrument during use may be needed, it would be preferable to have the resecting instrument remain axially stationary relative to the hysteroscope during use, particularly with windowed tubular resection instruments. What is needed therefore is a system that can allow the resecting instrument to rotate freely while inhibiting axial displacement relative to the hysteroscope to provide for effective resection and removal of fibroid and polyp tissue through the hysteroscope.

SUMMARY

The present invention provides methods for resecting and removing target tissue from a patient's body, such as fibroids, polyps and abnormal tissue from a uterus. The tissue is resected and captured in a probe, catheter, or other tissue-removal device, and expelled from the capture device by vaporizing a fluid, typically a liquid, adjacent to the captured tissue in order to propel the tissue from the device, typically through an extraction or other lumen present in a body or shaft of the device. Exemplary embodiments, the tissue removal device comprise a reciprocating blade or the like, where the blade may be advanced past a window on the device in order to resect a tissue strip and capture the strip within an interior volume or receptacle on the device. The liquid or other expandable fluid is also present in the device, and energy is applied to the fluid in order to cause rapid expansion, e.g., vaporization, in order to propel the severed tissue strip through the extraction lumen. In this way, the dimensions of the extraction lumen can be reduced, particularly in the distal regions of the device where size is of critical importance.

In a first aspect of the present invention, an improved hysteroscopic system comprises a hysteroscope having a main body coupled to an extension portion. The extension portion, typically a shaft, is configured to extend transcervically to a patient's uterine cavity. First, second, and third channels extend from the main body to a distal end of the extension portion, typically being formed inside of a tubular wall or structure of the extension portion. A fluid source is coupleable to a proximal end of the first channel, and a pressure sensor is coupleable to a proximal end of the second channel. A tissue resecting probe is configured for introduction through the third channel. At least one resistance feature is included which is configured to provide a selected level of resistance to axial sliding of the probe through the third channel while permitting rotation of the probe within the third channel.

The resistance feature may comprise a non-linear third channel, i.e., a third channel having a non-linear centerline. Typically, the non-linear centerline will be a curved centerline, and the curved centerline extends over a length in the range from 4 cm to 8 cm. The curved centerline will usually have a radius in the range from 150 mm to 900 mm. In other aspects, the curved centerline has a proximal end which is offset by a distance in the range from 2 mm to 5 mm from a hypothetical centerline of the third channel if it were straight.

Alternatively, the resistance feature may comprise detents formed in a wall of the shaft of the probe and detent-engaging elements within a component of the endoscope.

In other embodiments, the pressure sensor may be disposable. The second channel may have a cross-sectional area of greater than 0.5 mm$^2$, often greater than 1.0 mm$^2$.

The system of the present invention may further comprise a controller coupled to the fluid source and adapted to selectively control flows to the uterine cavity through the first channel at a rate between 0 ml/min and 750 ml/min. The controller may be coupled to the pressure sensor and may be adapted to selectively control pressure in the uterine cavity at any level between 0 mmHg and 150 mmHg. The controller may be further adapted to selectively control flows from the uterine cavity through the probe in the third channel at any rate between 0 ml/min and 750 ml/min.

In a second aspect of the present invention, a system for accessing a uterine cavity comprises an elongated body extending longitudinally about a first axis from a handle end through a shaft portion to a distal end. First, second and third channels extend from the handle end to a distal region of the shaft portion. A positive pressure fluid source is in communication with the first channel, and a pressure sensor is detachably coupled to a proximal end of the second channel. The third channel has a curved centerline and is configured for fluid outflows therethrough.

The system may further comprise a pressure relief valve in the handle end, and the third channel may be configured to receive an elongated tool.

In a third aspect of the present invention, a method for resecting fibroids or polyps in a uterus comprises transcervically introducing a distal end of an extension portion of a hysteroscope into the uterus. A resecting instrument is advanced through a curved channel of the hysteroscope so that a resecting end of the instrument extends form a distal end of the extension portion. The resecting end of the instrument is engaged against a fibroid or polyp while the instrument remains within the curved channel. The curve advantageously provides resistance to axial displacement of the resecting instrument shaft relative to the channel while the resecting end is engaged. The resistance, however, is such that the curve channel does not substantially inhibit rotation which is desirable.

BRIEF DESCRIPTION OF DRAWINGS

FIG. 8 is a schematic view of a distal end portion of another embodiment of inner RF resection sleeve.

FIG. 9A is a cross sectional view of the RF resection sleeve of FIG. 8 taken along line 9A-9A of FIG. 8.

FIG. 9B is a cross sectional view of the RF resection sleeve of FIG. 8 taken along line 9B-9B of FIG. 8.

DETAILED DESCRIPTION

Figure 1:
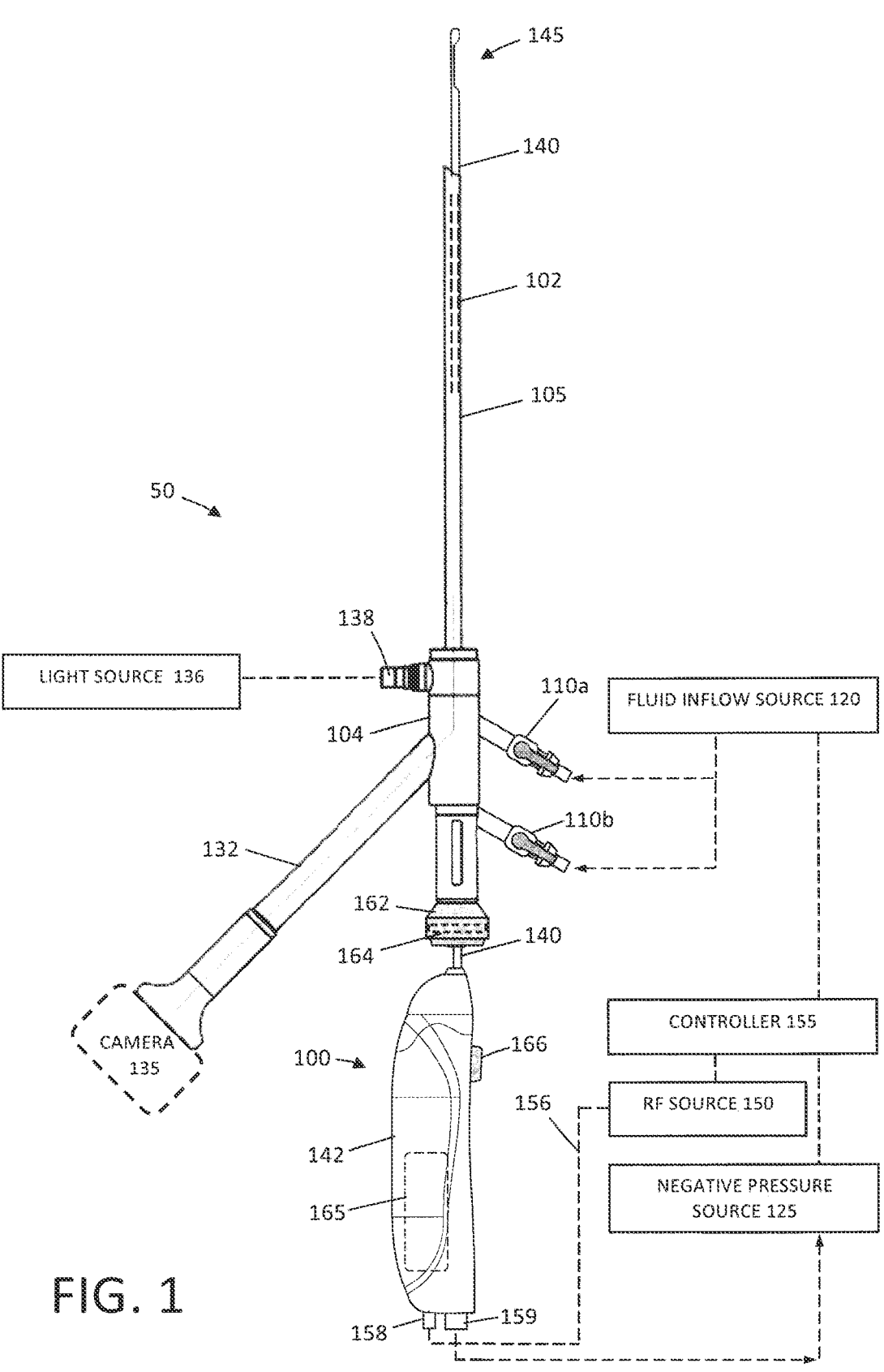
FIG. 1 is a plan view of an assembly including a hysteroscope and a tissue resecting device corresponding to the invention that is inserted through a working channel of the hysteroscope.
Figure 2:
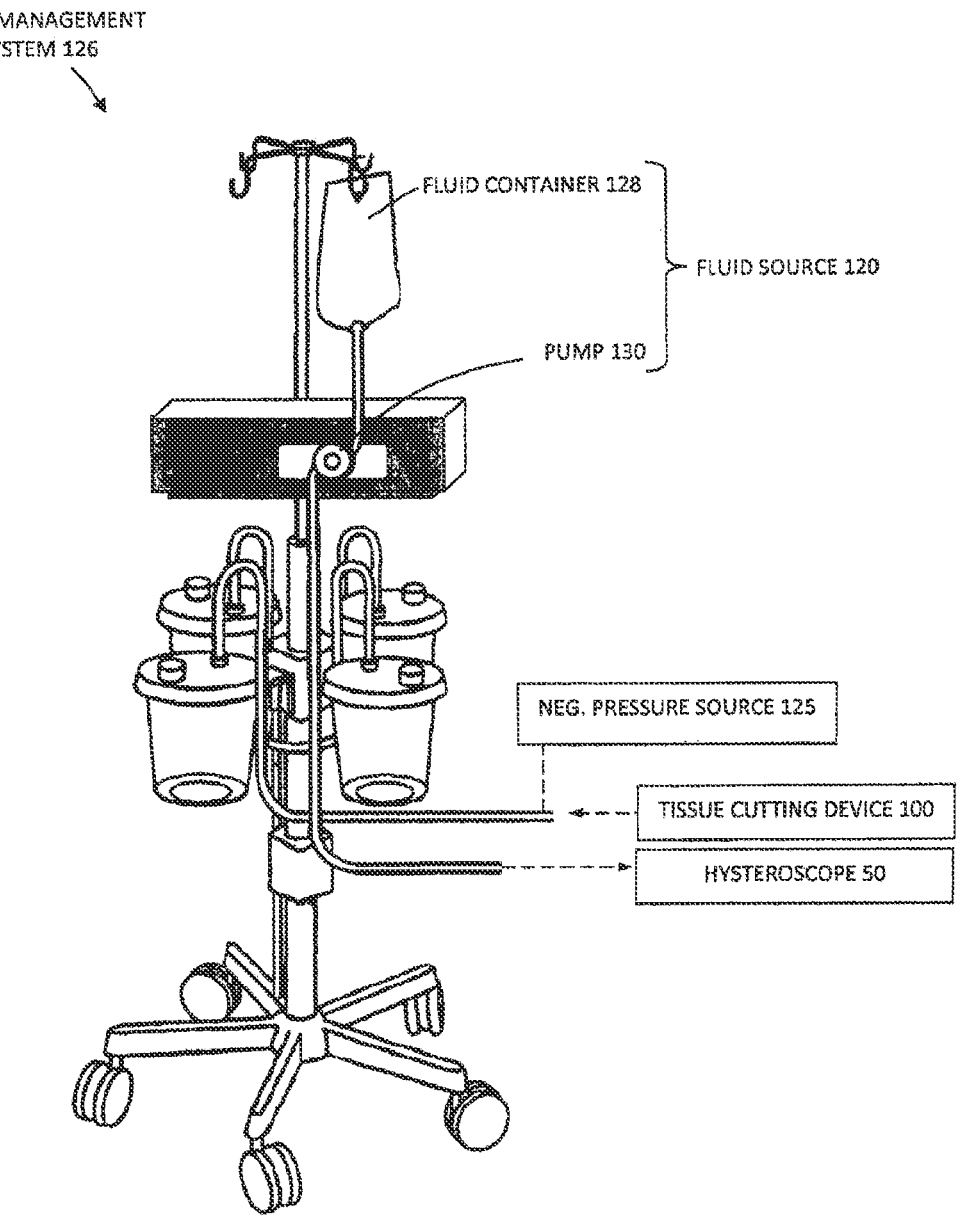
FIG. 2 is a schematic perspective view of a fluid management system used for distending the uterus and for assisting in electrosurgical tissue resection and extraction.

FIG. 1 illustrates an assembly that comprises an endoscope 50 used for hysteroscopy together with an electrosurgical tissue resecting device 100 extending through a working channel 102 of the endoscope. The endoscope or hysteroscope 50 has a handle 104 coupled to an elongated shaft 105 having a diameter of 5 mm to 7 mm. The working channel 102 therein may be round, D-shaped or any other suitable shape. The endoscope shaft 105 is further configured with an optics channel 106 and one or more fluid inflow/outflow channels 108a, 108b (FIG. 3) that communicate with valve-connectors 110a, 110b configured for coupling to a fluid inflow source 120 thereto, or optionally a negative pressure source 125 (FIGS. 1-2). The fluid inflow source 120 is a component of a fluid management system 126 as is known in the art (FIG. 2) which comprises a fluid container 128 and pump mechanism 130 which pumps fluid through the hysteroscope 50 into the uterine cavity. As can be seen in FIG. 2, the fluid management system 126 further includes the negative pressure source 125 (which can comprise an operating room wall suction source) coupled to the tissue resecting device 100. The handle 104 of the endoscope includes the angled extension portion 132 with optics to which a videoscopic camera 135 can be operatively coupled. A light source 136 also is coupled to light coupling 138 on the handle of the hysteroscope 50. The working channel 102 of the hysteroscope is configured for insertion and manipulation of the tissue resecting and extracting device 100, for example to treat and remove fibroid tissue. In one embodiment, the hysteroscope shaft 105 has an axial length of 21 cm, and can comprise a 0° scope, or 15° to 30° scope.

Still referring to FIG. 1, the tissue resecting device 100 has a highly elongated shaft assembly 140 configured to extend through the working channel 102 in the hysteroscope. A handle 142 of the tissue resecting device 100 is adapted for manipulating the electrosurgical working end 145 of the device. In use, the handle 142 can be manipulated both rotationally and axially, for example, to orient the working end 145 to resect targeted fibroid or polyp tissue. The tissue resecting device 100 has subsystems coupled to its handle 142 to enable electrosurgical resection of targeted tissue. A radiofrequency generator or RF source 150 and controller 155 are coupled to at least one RF electrode carried by the working end 145 as will be described in detail below. In one embodiment shown in FIG. 1, an electrical cable 156 and negative pressure source 125 are operatively coupled to a connectors 158 and 159 in handle 142. The electrical cable couples the RF source 150 to the electrosurgical working end 145. The negative pressure source 125 communicates with a tissue-extraction channel 160 in the shaft assembly 140 of the tissue extraction device 100 (FIG. 4).

FIG. 1 further illustrates a seal housing 162 that carries a flexible seal 164 carried by the hysteroscope handle 104 for sealing the shaft 140 of the tissue resecting device 100 in the working channel 102 to prevent distending fluid from escaping from a uterine cavity.

In one embodiment as shown in FIG. 1, the handle 142 of tissue resecting device 100 includes a motor drive 165 for reciprocating or otherwise moving a resecting component of the electrosurgical working end 145 as will be described below. The handle 142 optionally includes one or more actuator buttons 166 for actuating the device. In another embodiment, a footswitch can be used to operate the device. In one embodiment, the system includes a switch or control mechanism to provide a plurality of reciprocation speeds, for example 1 Hz, 2 Hz, 3 Hz, 4 Hz and up to 8 Hz. Further, the system can include a mechanism for moving and locking the reciprocating sleeve in a non-extended position and in an extended position. Further, the system can include a mechanism for actuating a single reciprocating stroke.

Figure 4:
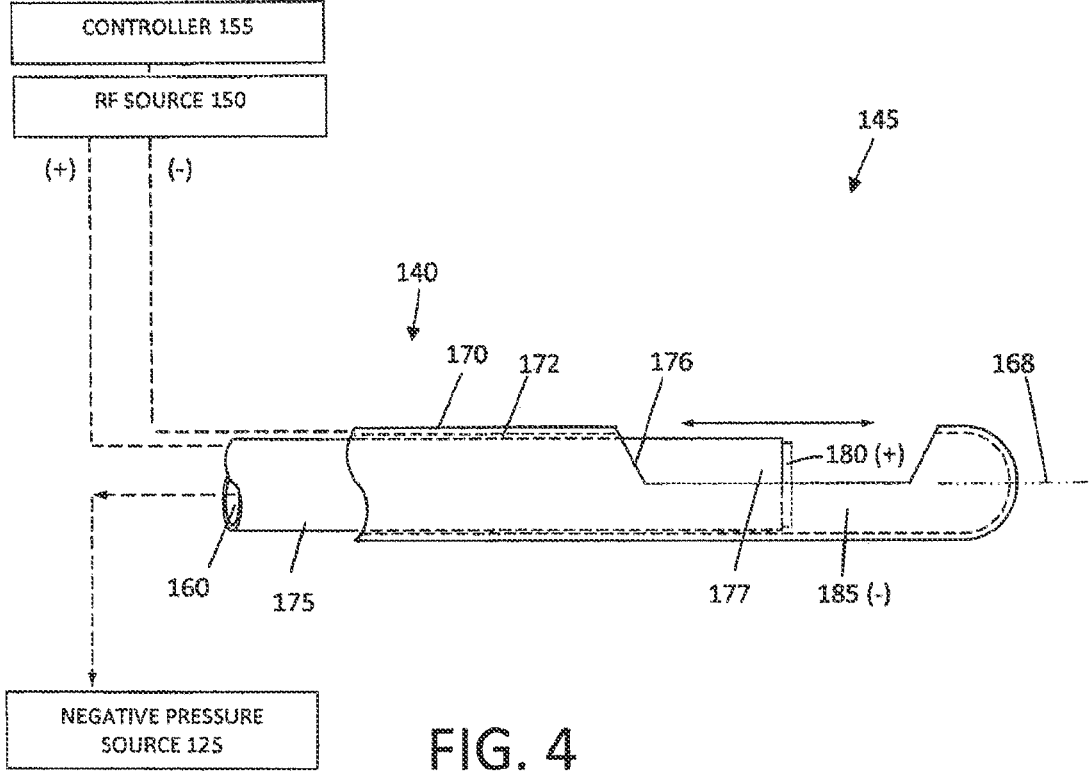
FIG. 4 is a schematic side view of the working end of the electrosurgical tissue resecting device of FIG. 1 showing an outer sleeve and a reciprocating inner sleeve and an electrode arrangement.

Referring to FIGS. 1 and 4, an electrosurgical tissue resecting device has an elongate shaft assembly 140 extending about longitudinal axis 168 comprising an exterior or first outer sleeve 170 with passageway or lumen 172 therein that accommodates a second or inner sleeve 175 that can reciprocate (and optionally rotate or oscillate) in lumen 172 to resect tissue as is known in that art of such tubular resection devices. In one embodiment, the tissue-receiving window 176 in the outer sleeve 170 has an axial length ranging between 10 mm and 30 mm and extends in a radial angle about outer sleeve 170 from about 45° to 210° relative to axis 168 of the sleeve. The outer and inner sleeves 170 and 175 can comprise a thin-wall stainless steel material and can function as opposing polarity electrodes as will be described in detail below. FIGS. 6A-8 illustrate insulating layers carried by the outer and inner sleeves 170 and 175 to limit, control and/or prevent unwanted electrical current flows between certain portions of the sleeve. In one embodiment, a stainless steel outer sleeve 170 has an O.D. of 0.143" with an I.D. of 0.133" and with an inner insulating layer (described below) the sleeve has a nominal I.D. of 0.125". In this embodiment, the stainless steel inner sleeve 175 has an O.D. of 0.120" with an I.D. of 0.112". The inner sleeve 175 with an outer insulating layer has a nominal O.D. of about 0.123" to 0.124" to reciprocate in lumen 172. In other embodiments, outer and or inner sleeves can be fabricated of metal, plastic, ceramic or a combination thereof. The cross-section of the sleeves can be round, oval or any other suitable shape.

As can be seen in FIG. 4, the distal end 177 of inner sleeve 175 comprises a first polarity electrode with distal resecting electrode edge 180 about which plasma can be generated. The electrode edge 180 also can be described as an active electrode during tissue resection since the electrode edge 180 then has a substantially smaller surface area than the opposing polarity or return electrode. In one embodiment in FIG. 4, the exposed surfaces of outer sleeve 170 comprises the second polarity electrode 185, which thus can be described as the return electrode since during use such an electrode surface has a substantially larger surface area compared to the functionally exposed surface area of the active electrode edge 180.

Figure 5:
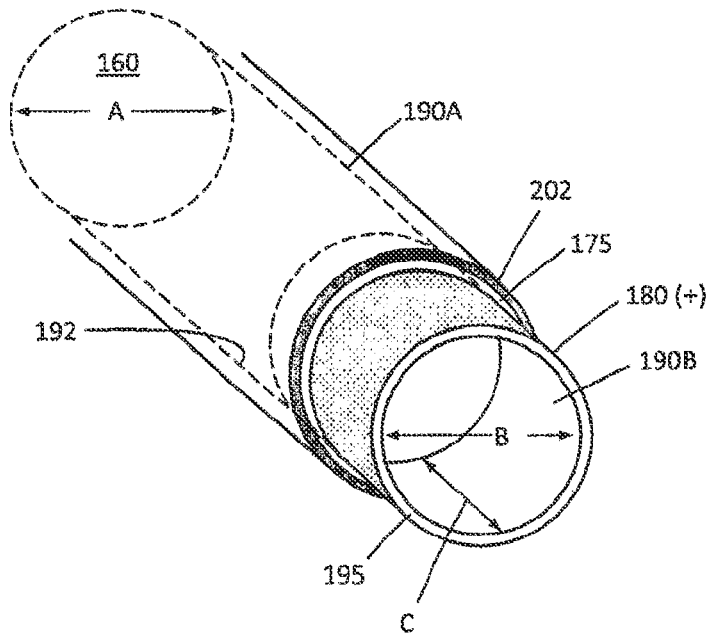
FIG. 5 is a schematic perspective view of the working end of the inner sleeve of FIG. 4 showing its electrode edge.
Figure 6A:
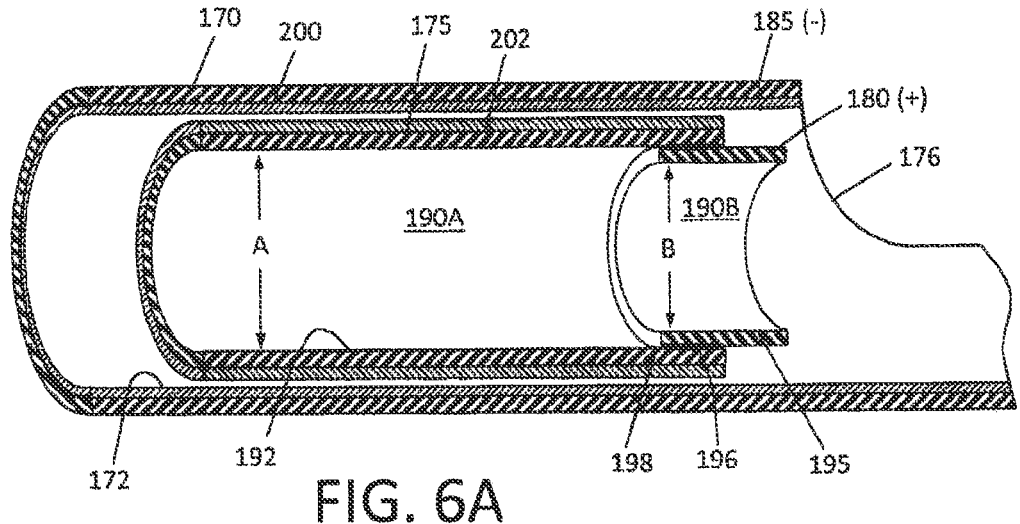
FIG. 6A is a schematic cut-away view of a portion of outer sleeve, inner RF resection sleeve and a tissue-receiving window of the outer sleeve.

In one aspect of the invention, the inner sleeve or resecting sleeve 175 has an interior tissue extraction lumen 160 with first and second interior diameters that are adapted to electrosurgically resect tissue volumes rapidly—and thereafter consistently extract the resected tissue strips through the highly elongated lumen 160 without clogging. Now referring to FIGS. 5 and 6A, it can be seen that the inner sleeve 175 has a first diameter portion 190A that extends from the handle 142 (FIG. 1) to a distal region 192 of the sleeve 175 wherein the tissue extraction lumen transitions to a smaller second diameter lumen 190B with a reduced diameter indicated at B which is defined by the electrode sleeve element 195 that provides the electrode edge 180. The axial length C of the reduced cross-section lumen 190B can range from about 2 mm to 20 mm. In one embodiment, the first diameter A is 0.112" and the second reduced diameter B is 0.100". As shown in FIG. 5, the inner sleeve 175 can be an electrically conductive stainless steel and the reduced diameter electrode portion also can comprise a stainless steel electrode sleeve element 195 that is welded in place by weld 196 (FIG. 6A). In another alternative embodiment, the electrode and reduced diameter electrode sleeve element 195 comprises a tungsten tube that can be press fit into the distal end 198 of inner sleeve 175. FIGS. 5 and 6A further illustrates the interfacing insulation layers 202 and 204 carried by the first and second sleeves 170, 175, respectively. In FIG. 6A, the outer sleeve 170 is lined with a thin-wall insulating material 200, such as PFA, or another material described below. Similarly, the inner sleeve 175 has an exterior insulating layer 202. These coating materials can be lubricious as well as electrically insulating to reduce friction during reciprocation of the inner sleeve 175.

The insulating layers 200 and 202 described above can comprise a lubricious, hydrophobic or hydrophilic polymeric material. For example, the material can comprise a bio-compatible material such as PFA, TEFLON®, polytetrafluroethylene (PTFE), FEP (fluorinated ethylenepropylene), polyethylene, polyamide, ECTFE (ethylenechlorotrifluoro-ethylene), ETFE, PVDF, polyvinyl chloride or silicone.

Figure 6B:
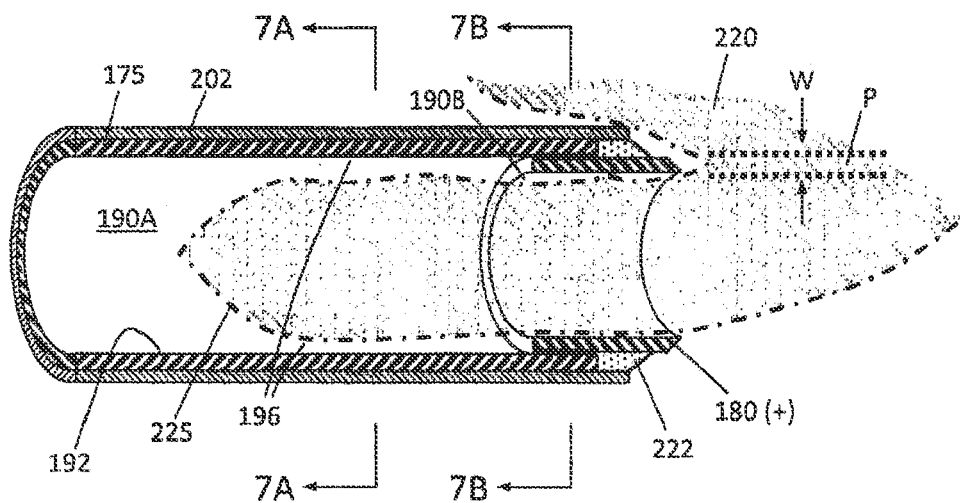
FIG. 6B is a schematic view of a distal end portion another embodiment of inner RF resection sleeve.

Now turning to FIG. 6B, another variation of inner sleeve 175 is illustrated in a schematic view together with a tissue volume being resected with the plasma electrode edge 180. In this embodiment, as in other embodiments in this disclosure, the RF source operates at selected operational parameters to create a plasma around the electrode edge 180 of electrode sleeve 195 as is known in the art. Thus, the plasma generated at electrode edge 180 can resect and ablate a path P in the tissue 220, and is suited for resecting fibroid tissue and other abnormal uterine tissue. In FIG. 6B, the distal portion of the inner sleeve 175 includes a ceramic collar 222 which is adjacent the distal edge 180 of the electrode sleeve 195. The ceramic 222 collar functions to confine plasma formation about the distal electrode edge 180 and functions further to prevent plasma from contacting and damaging the polymer insulating layer 202 on the inner sleeve 175 during operation. In one aspect of the invention, the path P in tissue 220 made with the plasma at electrode edge 180 provides a path P having an ablated width indicated at W, wherein such path width W is substantially wide due to tissue vaporization. This removal and vaporization of tissue in path P is substantially different than the effect of cutting similar tissue with a sharp blade edge, as in various prior art devices. A sharp blade edge can divide tissue (without cauterization) but applies mechanical force to the tissue and may prevent a large cross section slug of tissue from being cut. In contrast, the plasma at the electrode edge 180 can vaporize a path P in tissue without applying any substantial force on the tissue to thus resect larger cross sections or slugs strips of tissue. Further, the plasma ablation effect reduces the cross section of tissue strip 225 received in the tissue-extraction lumen 190B. FIG. 6B depicts a tissue strip to 225 entering lumen 190B which has such a smaller cross-section than the lumen due to the vaporization of tissue. Further, the cross section of tissue 225 as it enters the larger cross-section lumen 190A results in even greater free space 196 around the tissue strip 225. Thus, the resection of tissue with the plasma electrode edge 180, together with the lumen transition from the smaller cross-section (190B) to the larger cross-section (190A) of the tissue-extraction lumen 160 can significantly reduce or eliminate the potential for successive resected tissue strips 225 to clog the lumen. Prior art mechanical cutting devices with such small diameter tissue-extraction lumens typically have problems with tissue clogging.

In another aspect of the invention, the negative pressure source 225 coupled to the proximal end of tissue-extraction lumen 160 (see FIGS. 1 and 4) also can assist in aspirating and moving tissue strips 225 in the extraction lumen 160 in the proximal direction to a collection reservoir (not shown) outside the handle 142 of the device.

Figure 7A:
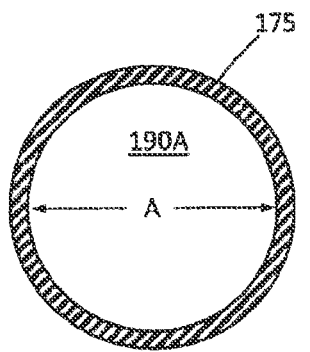
FIG. 7A is a cross sectional view of the inner RF resection sleeve of FIG. 6B taken along line 7A-7A of FIG. 6B.
Figure 7B:
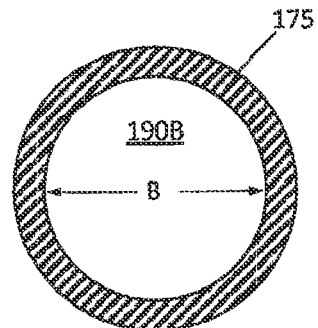
FIG. 7B is another cross sectional view of the inner RF resection sleeve of FIG. 6B taken along line 7B-7B of FIG. 6B.

FIGS. 7A-7B illustrate the change in lumen diameter of resection sleeve 175 of FIG. 6B. FIG. 8 illustrates the distal end of a variation of resection sleeve 175' which is configured with an electrode resection element 195' that is partially tubular in contrast to the previously described tubular electrode element 195 (FIGS. 5 and 6A). FIGS. 9A-9B again illustrate the change in cross-section of the tissue-extraction lumen between reduced cross-section region 190B' and the increased cross-section region 190A' of the resection sleeve 175' of FIG. 8. Thus, the functionality remains the same whether the resection electrode element 195' is tubular or partly tubular. In FIG. 8A, the ceramic collar 222' is shown, in one variation, as extending only partially around sleeve 175 to cooperate with the radial angle of resection electrode element 195'. Further, the variation of FIG. 8 illustrates that the ceramic collar 222' has a larger outside diameter than insulating layer 202. Thus, friction may be reduced since the short axial length of the ceramic collar 222' interfaces and slides against the interfacing insulating layer 200 about the inner surface of lumen 172 of outer sleeve 170.

In general, one aspect of the invention comprises a tissue resecting and extracting device (FIGS. 10A-11C) that includes first and second concentric sleeves having an axis and wherein the second (inner) sleeve 175 has an axially-extending tissue-extraction lumen therein, and wherein the second sleeve 175 is moveable between axially non-extended and extended positions relative to a tissue-receiving window 176 in first sleeve 170 to resect tissue, and wherein the tissue extraction lumen 160 has first and second cross-sections. The second sleeve 175 has a distal end configured as a plasma electrode edge 180 to resect tissue disposed in tissue-receiving window 176 of the first sleeve 170. Further, the distal end of the second sleeve, and more particularly, the electrode edge 180 is configured for plasma ablation of a substantially wide path in the tissue. In general, the tissue-extraction device is configured with a tissue extraction lumen 160 having a distal end portion with a reduced cross-section that is smaller than a cross-section of medial and proximal portions of the lumen 160.

In one aspect of the invention, referring to FIGS. 7A-7B and 9A-9B, the tissue-extraction lumen 160 has a reduced cross-sectional area in lumen region 190A proximate the plasma tip or electrode edge 180 wherein said reduced cross section is less that 95%, 90%, 85% or 80% than the cross sectional area of medial and proximal portions 190B of the tissue-extraction lumen, and wherein the axial length of the tissue-extraction lumen is at least 10 cm, 20 cm, 30 cm or 40 cm. In one embodiment of tissue resecting device 100 for hysteroscopic fibroid resection and extraction (FIG. 1), the shaft assembly 140 of the tissue resecting device is 35 cm in length.

Figures 10A, 10B, 10C:
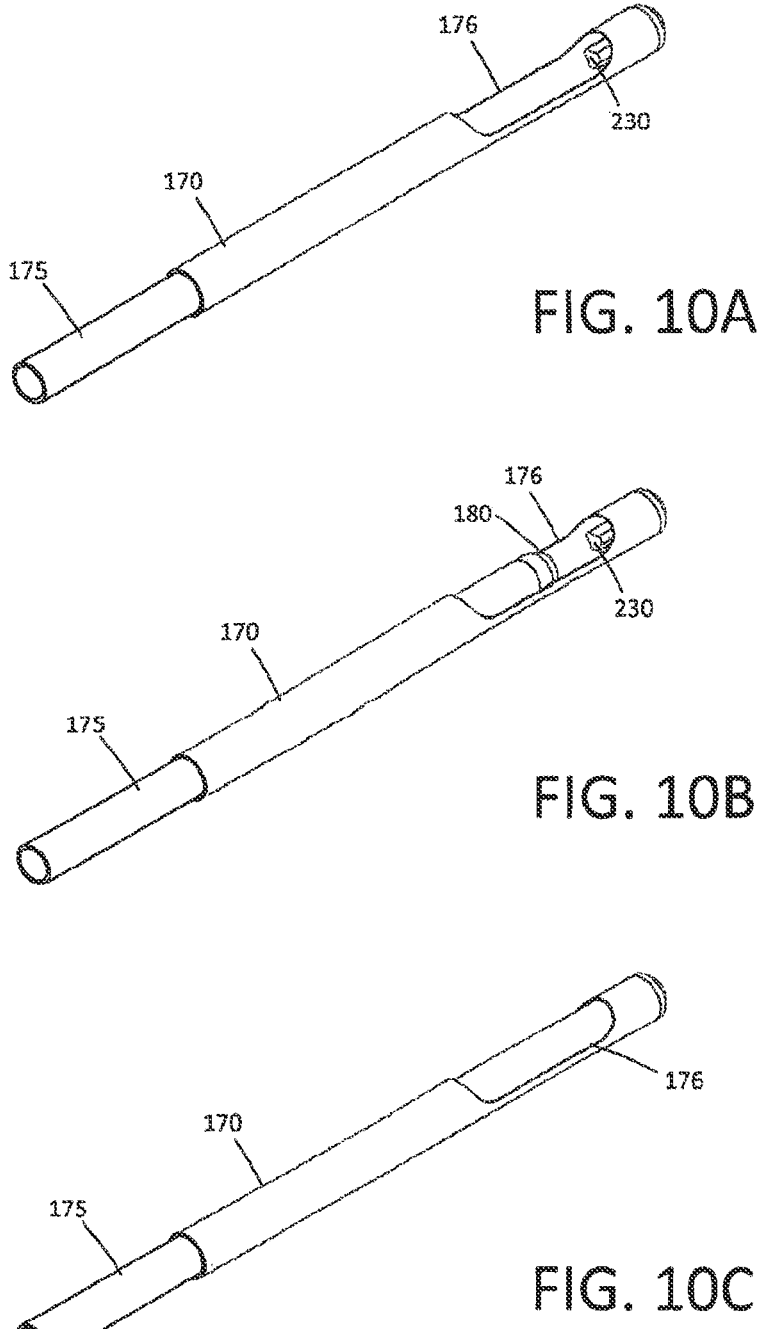
FIG. 10A is a perspective view of the working end of the tissue resecting device of FIG. 1 with the reciprocating RF resection sleeve in a non-extended position.
FIG. 10B is a perspective view of the tissue resecting device of FIG. 1 with the reciprocating RF resection sleeve in a partially extended position.
FIG. 10C is a perspective view of the tissue resecting device of FIG. 1 with the reciprocating RF resection sleeve in a fully extended position across the tissue-receiving window.
Figures 11A, 11B, 11C:
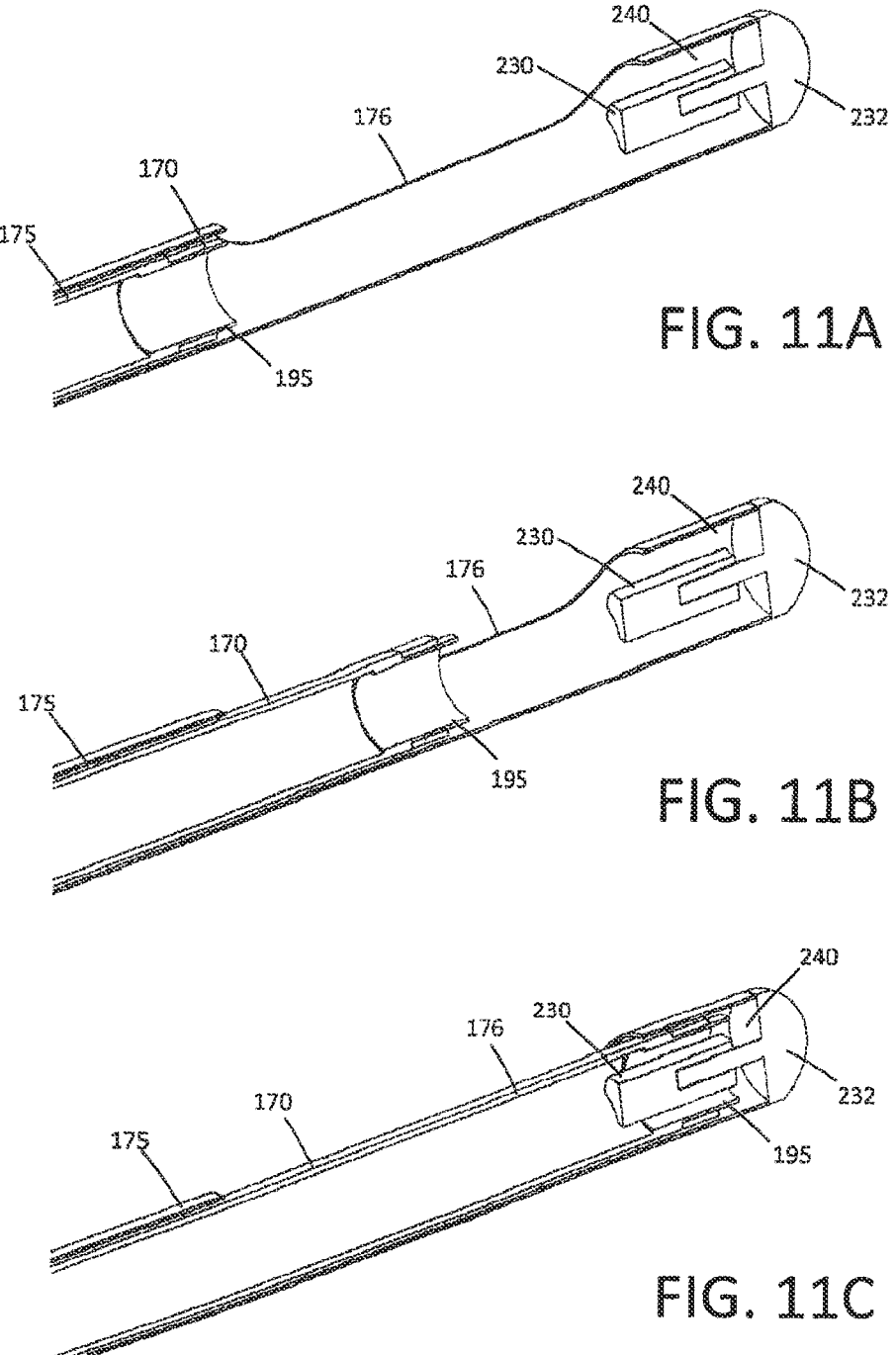
FIG. 11A is a sectional view of the working end of the tissue resecting device of FIG. 10A with the reciprocating RF resection sleeve in a non-extended position.
FIG. 11B is a sectional view of the working end of FIG. 10B with the reciprocating RF resection sleeve in a partially extended position.
FIG. 11C is a sectional view of the working end of FIG. 10C with the reciprocating RF resection sleeve in a fully extended position.

FIGS. 10A-10C illustrate the working end 145 of the tissue resecting device 100 with the reciprocating resecting sleeve or inner sleeve 175 in three different axial positions relative to the tissue receiving window 176 in outer sleeve 170. In FIG. 10A, the resecting sleeve 175 is shown in a retracted or non-extended position in which the sleeve 175 is at it proximal limit of motion and is prepared to advance distally to an extended position to thereby electrosurgically resect tissue positioned in and/or suctioned into in window 176. FIG. 10B shows the inner sleeve 175 moved and advanced distally to a partially advanced or medial position relative to tissue receiving window 176. FIG. 10C illustrates the inner sleeve 175 fully advanced and extended to the distal limit of its motion wherein the plasma ablation electrode 180 has extended past the distal end 226 of tissue-receiving window 176 at which moment the resected tissue strip 225 is excised from tissue volume 220 and captured in reduced cross-sectional lumen region 190A.

Now referring to FIGS. 10A-10C, FIGS. 11A-11C and FIGS. 12A-12C, another aspect of the invention comprises "tissue displacement" mechanisms provided by multiple elements and processes to "displace" and move tissue strips 225 (FIG. 12A) in the proximal direction in lumen 160 of inner sleeve 175 to thus ensure that tissue does not clog the lumen of the inner sleeve 175. As can be seen in FIG. 10A and the enlarged views of FIGS. 11A-11C, one tissue displacement mechanism comprises a projecting element 230 that extends proximally from distal tip 232 which is fixedly attached to outer sleeve 170. The projecting element 230 extends proximally along central axis 168 in a distal chamber 240 defined by outer sleeve 170 and distal tip 232. In one embodiment depicted in FIG. 11A, the shaft-like projecting element 230, in a first functional aspect, comprises a mechanical pusher that functions to push a captured tissue strip 225 proximally from the small cross-section lumen 190B of inner sleeve 175 (FIG. 12A) as the inner sleeve 175 moves to its fully advanced or extended position.

Figure 12A:
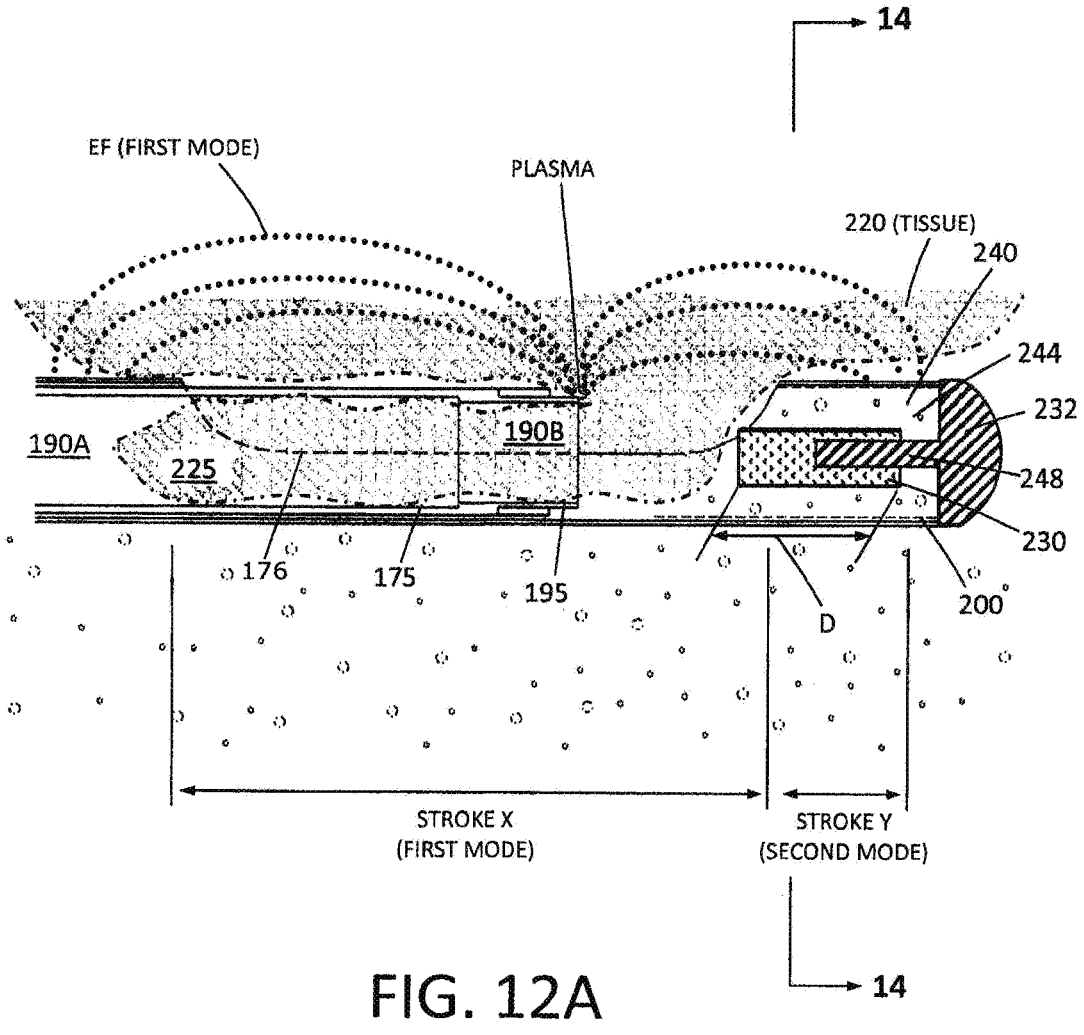
FIG. 12A is an enlarged sectional view of the working end of tissue resecting device of FIG. 11B with the reciprocating RF resection sleeve in a partially extended position showing the RF field in a first RF mode and plasma resection of tissue.
Figure 12B:
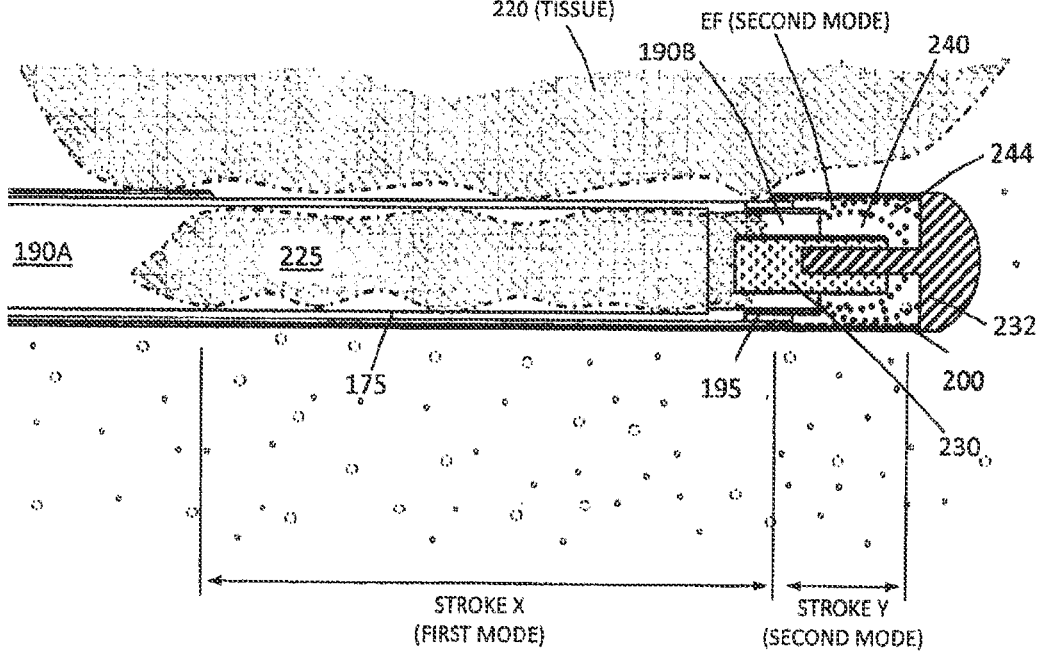
FIG. 12B is an enlarged sectional view of the working end of FIG. 11C with the reciprocating RF resection sleeve almost fully extended and showing the RF fields switching to a second RF mode from a first RF mode shown in FIG. 12.
Figure 12C:
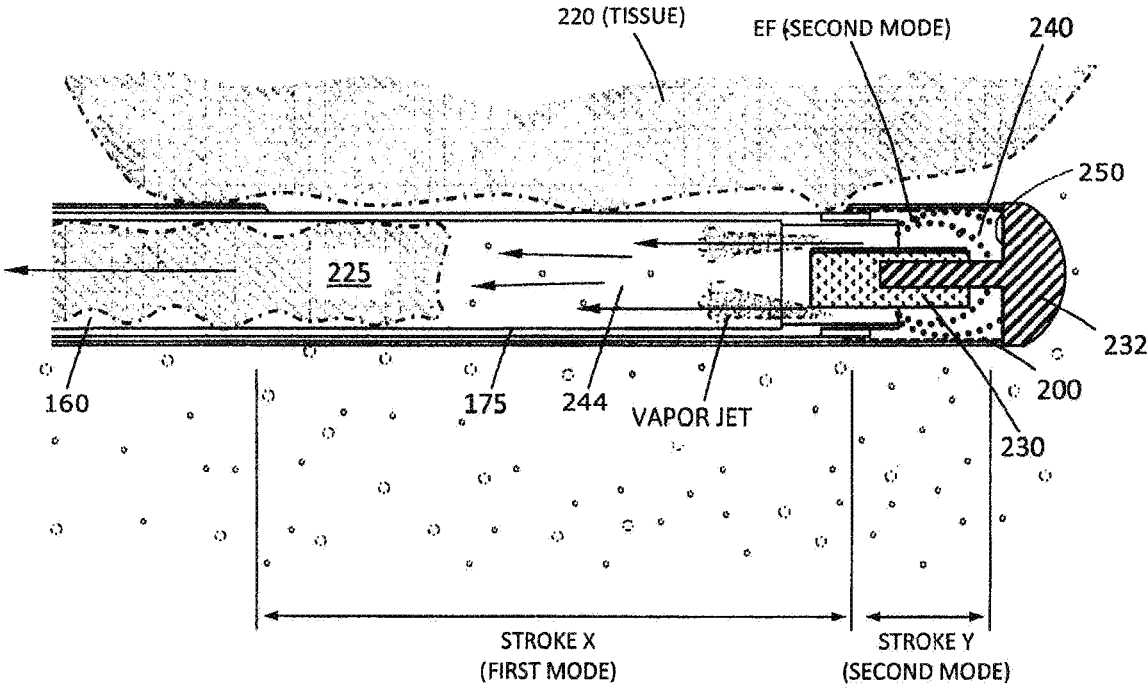
FIG. 12C is an enlarged sectional view of the working end of FIG. 11C with the reciprocating RF resection sleeve again almost fully extended and showing the explosive vaporization of a captured liquid volume to expel resected tissue in the proximal direction.

In a second functional aspect, the chamber 240 in the distal end of sleeve 170 is configured to capture a volume of saline distending fluid 244 (FIG. 12A) from the working space, and wherein the existing RF electrodes of the working end 145 are further configured to explosively vaporize the captured fluid 244 to generate proximally-directed forces on tissue strips 225 resected and disposed in lumen 160 of the inner sleeve 175 (FIGS. 12B and 12C). Both of these functional elements and processes (tissue displacement mechanisms) can apply a substantial mechanical force on the captured tissue strips 225 by means of the explosive vaporization of liquid in chamber 240 and can function to move tissue strips 225 in the proximal direction in the tissue-extraction lumen 160. It has been found that using the combination of multiple functional elements and processes can virtually eliminate the potential for tissue clogging the tissue extraction lumen 160.

More particularly, FIGS. 12A-12C illustrate the functional aspects of the tissue displacement mechanisms and the subsequent explosive vaporization of fluid captured in chamber 240. In FIG. 12A, the reciprocating inner sleeve 175 is shown in a medial position advancing distally wherein plasma at the resecting electrode edge 180 is resecting a tissue strip 225 that is disposed within lumen 160 of the inner sleeve 175. In FIG. 12A-12C, it can be seen that the system operates in first and second electrosurgical modes corresponding to the reciprocation and axial range of motion of inner sleeve 175 relative to the tissue-receiving window 176. As used herein, the term "electrosurgical mode" refers to which electrode of the two opposing polarity electrodes functions as an "active electrode" and which electrode functions as a "return electrode". The terms "active electrode" and "return electrode" are used in accordance with convention in the art—wherein an active electrode has a smaller surface area than the return electrode which thus focuses RF energy density about such an active electrode. In the working end 145 of FIGS. 10A-11C, the resecting electrode element 195 and its electrode edge 180 must comprise the active electrode to focus energy about such electrode to generate the plasma for tissue resection. Such a high-intensity, energetic plasma at the electrode edge 180 is needed throughout stroke X indicated in FIG. 12A-12B to resect tissue. The first mode occurs over an axial length of travel of inner sleeve 175 as it crosses the tissue-receiving window 176, at which time the entire exterior surface of outer sleeve 170 comprises the return electrode indicated at 185. The electrical fields EF of the first RF mode are indicated generally in FIG. 12A.

FIG. 12B illustrates the moment in time at which the distal advancement or extension of inner sleeve 175 entirely crosses the tissue-receiving window 176 (FIG. 12A). At this time, the electrode sleeve 195 and its electrode edge 180 are confined within the mostly insulated-wall chamber 240 defined by the outer sleeve 170 and distal tip 232. At this moment, the system is configured to switch to the second RF mode in which the electric fields EF switch from those described previously in the first RF mode. As can be seen in FIG. 12B, in this second mode, the limited interior surface area 250 (FIG. 12C) of distal tip 232 that interfaces chamber 240 functions as an active electrode and the distal end portion of inner sleeve 175 exposed to chamber 240 acts as a return electrode. In this mode, very high energy densities occur about surface 250 and such a contained electric field EF can explosively and instantly vaporize the fluid 244 captured in chamber 240. The expansion of water vapor can be dramatic and can thus apply tremendous mechanical forces and fluid pressure on the tissue strip 225 to move the tissue strip in the proximal direction in the tissue extraction lumen 160. FIG. 12C illustrates such explosive or expansive vaporization of the distention fluid 244 captured in chamber 240 and further shows the tissue strip 225 being expelled in the proximal direction the lumen 160 of inner sleeve 175.

Figure 14:
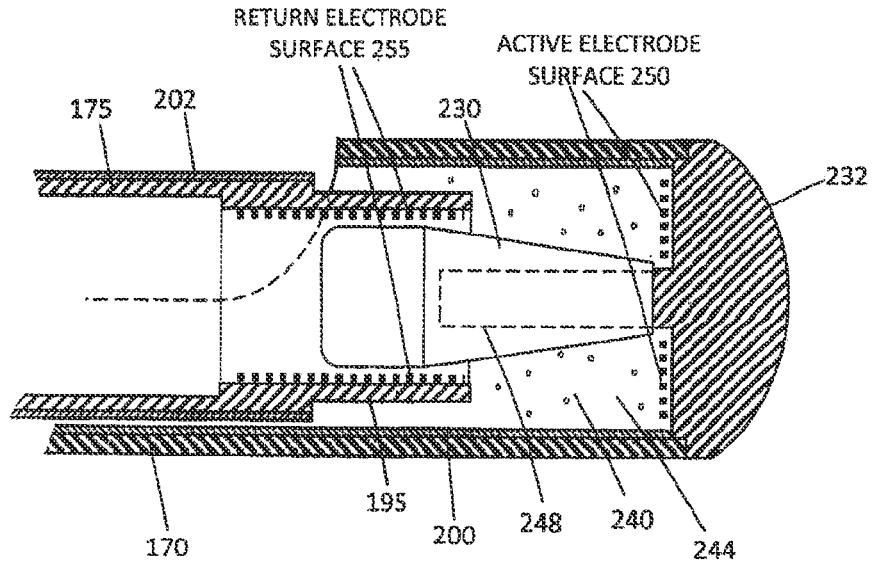
FIG. 14 is a sectional view of the working end of FIG. 12C showing an interior chamber and a variation of a projecting element.

FIG. 14 shows the relative surface areas of the active and return electrodes at the extended range of motion of the inner sleeve 175, again illustrating that the surface area of the non-insulated distal end surface 250 is small compared to surface 255 of electrode sleeve which comprises the return electrode.

Still referring to FIGS. 12A-12C, it has been found that a single power setting on the RF source 150 and controller 155 can be configured both (i) to create plasma at the electrode edge 180 of electrode sleeve 195 to resect tissue in the first mode, and (ii) to explosively vaporize the captured distention fluid 244 in the second mode. Further, it has been found that the system can function with RF mode-switching automatically at suitable reciprocation rates ranging from 0.5 cycles per second to 8 or 10 cycles per second. In bench testing, it has been found that the tissue resecting device described above can resect and extract tissue at the rate of from 4 grams/min to 8 grams/min without any potential for tissue strips 225 clogging the tissue-extraction lumen 160. In these embodiments, the negative pressure source 125 also is coupled to the tissue-extraction lumen 160 to assist in applying forces for tissue extraction.

Of particular interest, the fluid-capture chamber 240 defined by sleeve 170 and distal tip 232 can be designed to have a selected volume, exposed electrode surface area, length and geometry to optimize the application of expelling forces to resected tissue strips 225. In one embodiment, the diameter of the chamber is 3.175 mm and the length is 5.0 mm which taking into account the projecting element 230, provided a captured fluid volume of approximately 0.040 mL. In other variations, the captured fluid volume can range from 0.004 mL to 0.080 mL.

In one example, a chamber 240 with a captured liquid volume of 0.040 mL together with 100% conversion efficiency in and instantaneous vaporization would require 103 Joules to heat the liquid from room temperature to water vapor. In operation, since a Joule is a W*s, and the system reciprocate at 3 Hz, the power required would be on the order of 311 W for full, instantaneous conversion to water vapor. A corresponding theoretical expansion of 1700× would occur in the phase transition, which would result in up to 25,000 psi instantaneously (14.7 psi×1700), although due to losses in efficiency and non-instantaneous expansion, the actual pressures would be much less. In any event, the pressures are substantial and can apply significant expelling forces to the captured tissue strips 225.

Referring to FIG. 12A, the interior chamber 240 can have an axial length from about 0.5 mm to 10 mm to capture a liquid volume ranging from about 0.004 mL 0.01 mL. It can be understood in FIG. 12A, that the interior wall of chamber 240 has an insulator layer 200 which thus limits the electrode surface area 250 exposed to chamber 240. In one embodiment, the distal tip 232 is stainless steel and is welded to outer sleeve 170. The post element 248 is welded to tip 232 or machined as a feature thereof. The projecting element 230 in this embodiment is a non-conductive ceramic.

Figure 13:
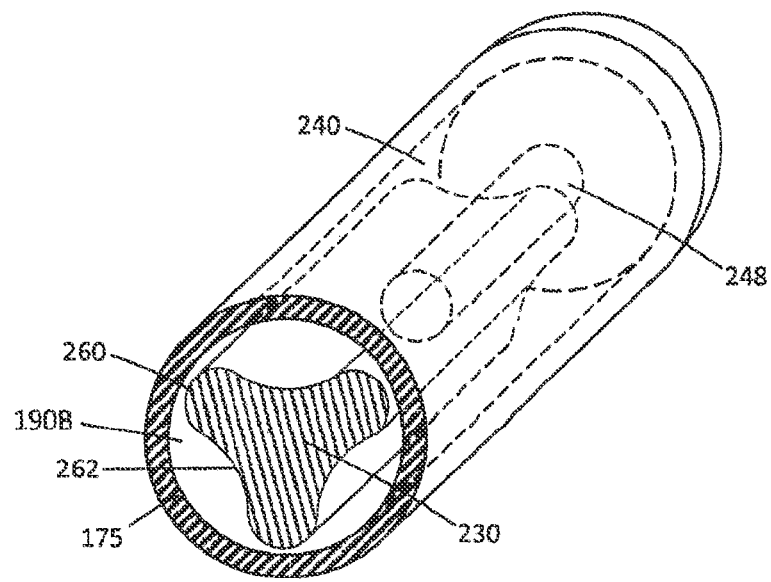
FIG. 13 is an enlarged perspective view of a portion of the working end of FIG. 12C showing an interior chamber and a fluted projecting element.

FIG. 13 shows the cross-section of the ceramic projecting element 230 which may be fluted, and which in one embodiment has three flute elements 260 and three corresponding axial grooves 262 in its surface. Any number of flutes, channels or the like is possible, for example from two to about 20. The fluted design increases the available cross-sectional area at the proximal end of the projecting element 230 to push the tissue strip 225, while at the same time the three grooves 262 permit the proximally-directed jetting of water vapor to impact the tissue exposed to the grooves 262. In one embodiment, the axial length D (FIG. 12A) of the projecting element 230 is configured to push tissue entirely out of the reduced cross-sectional region 190B of the electrode sleeve element 195. In another embodiment, the volume of the chamber 240 is configured to capture liquid that when explosively vaporized provided a gas (water vapor) volume sufficient to expand into and occupy at least the volume defined by a 10% of the total length of extraction channel 160 in the device, usually at least 20% of the extraction channel 160, often at least 40% of the extraction channel 160, sometimes at least 60% of the extraction channel 160, other times at least 80% of the extraction channel 160, and sometimes at least 100% of the extraction channel 160.

As can be understood from FIGS. 12A to 12C, the distending fluid 244 in the working space replenishes the captured fluid in chamber 240 as the inner sleeve 175 moves in the proximal direction or towards its non-extended position. Thus, when the inner sleeve 175 again moves in the distal direction to resect tissue, the interior chamber 240 is filled with fluid 244 which is then again contained and is then available for explosive vaporization as described above when the inner sleeve 175 closes the tissue-receiving window 176. In another embodiment, a one-way valve can be provided in the distal tip 232 to draw fluid directly into interior chamber 240 without the need for fluid to migrate through window 176.

In another embodiment, the RF source 150 and controller 155 can be programmed to modulate energy delivery parameters during stroke X and stroke Y in FIGS. 12A-12C to provide the optimal energy (i) for plasma resection with electrode edge 180, and (ii) for explosively vaporizing the captured fluid in chamber 240.

It should be appreciated that while an RF source is suitable for causing explosive vaporization of the captured fluid volume, any other energy source can be used and falls within the scope of the invention, such as an ultrasound transducer, HIFU, a laser or light energy source, a microwave or a resistive heat source.

Figure 15:
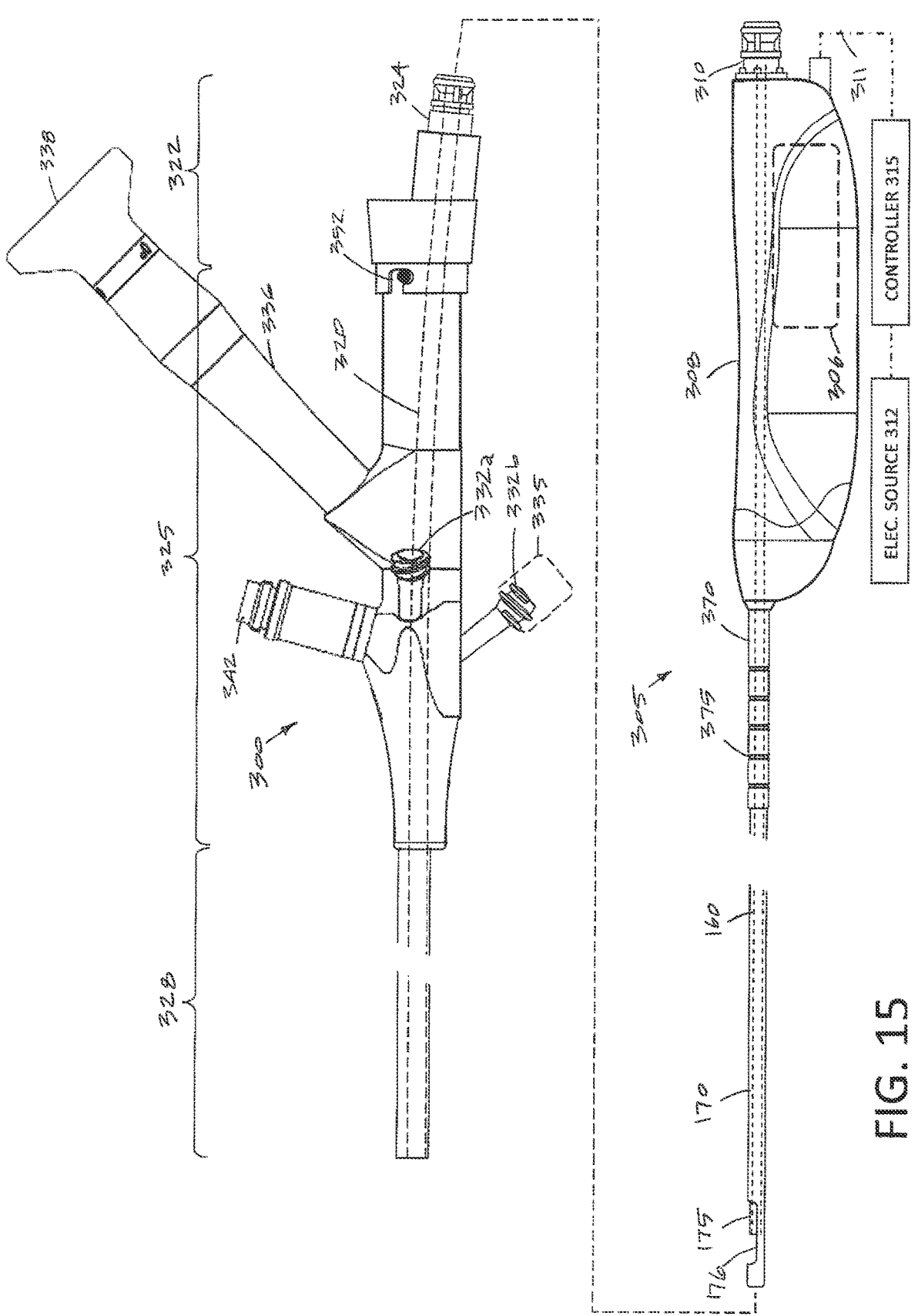
FIG. 15 is a plan view of another fibroid removal system including an endoscope and an electrosurgical tissue resecting device that is inserted through a curved working channel of the hysteroscope.

FIG. 15 is a side view of a fibroid removal system similar to that of FIG. 1 that includes an endoscope 300 configured for use in hysteroscopy and an RF tissue resecting device 305 configured for introduction through the working channel in the endoscope 300.

In FIG. 15, it can be seen that the resecting device has inner and outer sleeves 170 and 175 with the inner sleeve 175 reciprocated axially relative to window 176 by a motor 306 in handle 308. The tissue extraction channel 160 in the inner sleeve 175 extends through the handle 308 in communication with a quick-connect fitting 310. A negative pressure source coupled to a flexible extraction tubing (not shown) can be connected to fitting 310 to thereby carry resected tissue and fluid to a collection reservoir (cf. FIG. 1). The motor 306 is coupled to an electrical cable 311 that extends to an electrical source 312 and controller 315.

Figure 3:
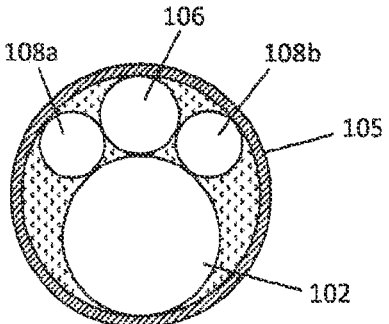
FIG. 3 is a cross-sectional view of the shaft of the hysteroscope of FIG. 1 showing various channels therein.
Figure 16:
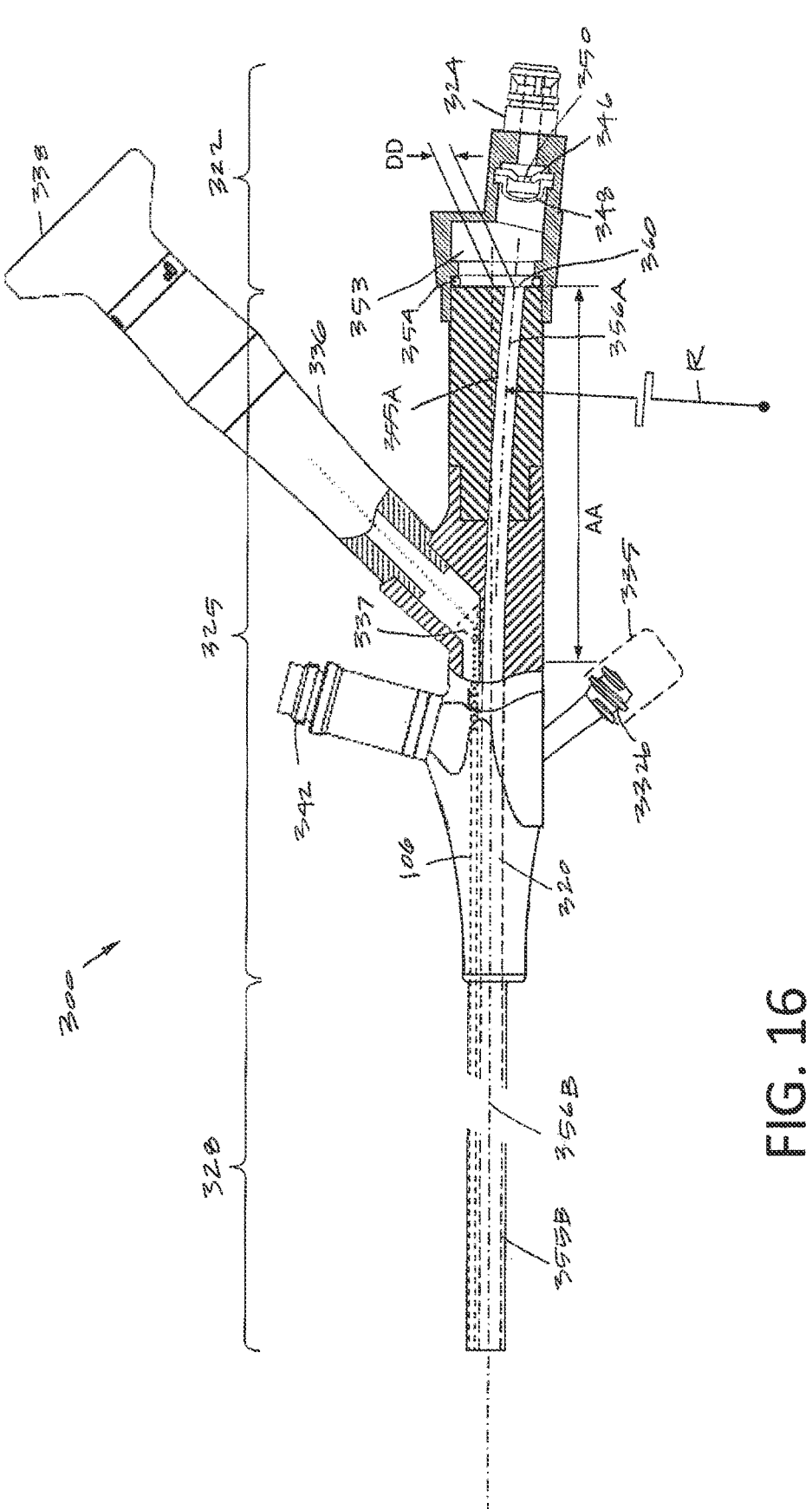
FIG. 16 is a cut-away view of the hysteroscope of FIG. 15 showing a disposable adapter component carrying a seal assembly and further showing a working channel with a curved portion in the main body of the endoscope.

In FIGS. 15 and 16, it can be seen that the endoscope 300 is similar to the endoscope of FIGS. 1 and 3, except that endoscope 300 in FIGS. 15-16 differs in that (i) the endoscope has a different configuration of working channel 320 which is curved to provide a pre-determined resistance to sliding a resecting tool shaft in the channel, and (ii) the endoscope has a different type of disposable adapter component 322 that carries a quick-connect fitting 324 for purposes described below.

More in particular, FIGS. 15-16 show that endoscope 300 has a handle or main body 325 of a metal that is coupled to an extension or shaft portion 328. The elongated shaft 328 can have a diameter ranging from 5 mm to 10 mm and in one embodiment is 6.2 mm. The endoscope shaft 328 has an axial length of 15 to 35 cm and the endoscope 300 can be a 0° scope, or 15° to 30° scope.

The endoscope shaft 328 has an optics channel 106 and first and second fluid flow channels 108a and 108b as shown in the endoscope of FIG. 3. The flow channels 108a and 108b (FIG. 3) communicate with Luer connectors 332a and 332b (see FIGS. 15-16). A fluid inflow source 120 (FIG. 2) is coupled to first connector 332a and channel 108a. A pressure sensor 335 is coupled to second connector 332b and channel 108b. The pressure sensor 335 is adapted to measure actual intracavity pressure (as described further below) and to send pressure signals continuously to controller 315.

The main body 325 of the endoscope 300 includes the angled extension portion 336 with optics and prism 337 which provides light path LP to thereby allow viewing through optics channel 106. A videoscopic camera can be coupled to the proximal end 338 of the angled extension portion 336. A light source is coupled to light connector 342 on the main body 325 of the endoscope.

In FIGS. 15-16, it can be see that the endoscope 300 includes a detachable and disposable adapter component 322 that carries first and second seals 346 and 348 that are configured to seal the working channel 320 when there is a resecting tool shaft in the channel or in the absence of a shaft in the channel 320. The more distal seal 348 can comprise a duck-bill seal or its equivalent that seals the channel when there is no tool shaft in channel 320. The more proximal seal 346 comprises an elastomeric seal with port 350 that can stretch and impinge on a tool shaft disposed in the channel 322. In one variation shown in FIG. 16, the disposable component 322 can molded of plastic and can be detachably coupled to main body 325 of the endoscope by a J-lock 352. An o-ring 354 can be provided in an interface between the main body 325 and the disposable component 322. Any suitable fitting can be used to couple the disposable component 322 to the main body 325 such as threads, J-locks, etc. FIG. 16 further shows that the disposable adapter component 322 has an interior chamber 353 that has a substantial fluid volume which can optionally be configured with a manual or automated pressure relief valve as will be further described below in related embodiments.

Referring again to FIGS. 15 and 16, it has been found that the curved portion 355A of the working channel 322 functions to provide resistance to unwanted axial sliding of a resecting tool shaft when in use, while at the same time not providing any resistance to rotation of the resecting device shaft. In use, the electrosurgical resecting device 305 as generally shown in FIGS. 1, 4, 10A-14 and 15 is manipulated to resect tissue only by pressing the working end window 176 into a targeted tissue site together with slight rotation of the working end while resecting tissue. During use, the working end of the RF resecting device of FIG. 15 should not be moved axially back and forth to resect tissue channel as is typical with commercially available RF resecting loops known in the prior art. For this reason, the configuration of curved working channel 355A shown in FIGS. 15-16 provides a desired increase in resistance to axial sliding of the resecting device shaft in the endoscope which assists in preventing physicians from using the combination of the present invention (RF resecting device and endoscope) in the manner commonly associated with prior art RF resecting loops. The shaft of the RF resecting device 305 is also configured to be suitably flexible to cooperate with the curved working channel. It has been found that a curved working channel as described herein does not interfere with the physician's rotation of the resecting device shaft in the working channel 322, which also is advantageous.

In FIGS. 15 and 16, an embodiment of endoscope 300 has a working channel 322 that has a curved or non-straight portion 355A with curved axis 356A that extends through main body 325 and a straight channel portion 355B with straight axis 356B that extends longitudinally through the shaft portion 328 of the endoscope. The curved channel portion 355A can extend over a length AA ranging from about 4 cm to 8 cm and in one embodiment is about 5 cm. The curved channel portion 355A can have a radius R ranging from about 150 mm to 900 mm. In one embodiment, the central axis 356A of the curved channel portion 355A at the proximal face 360 of main body 325 is offset by a distance having dimension DD which can be about 2 mm to 5 mm (see FIG. 16) from the hypothetical central axis 355B of the straight channel portion 355B if extended to the proximal face 360 of main body 325. In one embodiment, the offset dimension DD is 2.0 mm. In an embodiment, the surface of a least the curved channel portion 355A in the metal main body 325 can have a coating of titanium nitride or gold which can protect the channel from damage over the working life of the endoscope.

In another embodiment (not shown), the working channel 322 in an endoscope 300 similar to that of FIG. 15 can be straight or curved and an alternative mechanism can be used to provide resistance to axial sliding of a tool shaft. In one variation, a compression assembly known in the art can be used to squeeze an interference element against the tool shaft in the working channel, such as radial inward compression of an O-ring. FIG. 15 illustrates another mechanism that may be used to indicate or resist axial sliding of a tool shaft in the working channel. As can be seen in FIG. 15, the RF resecting device has a stiffener sleeve 370 disposed around the proximal end 372 of outer sleeve 170. The stiffener sleeve 370 can have a length of 4 to 6 cm and is configured with 5 to 50 annular grooves or detents 375 that cooperate with a spring element (not shown) in the adapter component 322 for engaging the detents 375 to provide tactile feedback to the physician relating to axial sliding of the tool shaft.

In general, the endoscope 300 comprises a main body 325 and extended shaft portion 328 that extends longitudinally to a distal end, a first channel extending from the handle end to the distal end coupleable to a fluid inflow source, a second channel extending from the handle end to the distal end configured for fluid outflows and/or receiving an RF resecting device, wherein the second channel has first straight portion and a second curved portion, and a disposable component carrying at least one seal detachably coupled to the endoscope main body and the second channel. In one variation, the device has first and second seals elements carried in the disposable component configured to seal the second channel with or without a tool shaft disposed therein. In one variation, a third channel is configured for coupling to a pressure sensor 335 (see FIGS. 15-16). A fourth channel is configured as an optics channel for viewing the uterine cavity A fifth channel is configured as a light guide extending from the main body of the endoscope to the distal end of the extended shaft portion 328. The endoscope can have a pressure sensor 335 that is configured to send pressure signals to a controller 315 to control fluid inflows and fluid outflows through the endoscope to thereby control fluid pressure in the uterine cavity. The controller can be operatively coupled to the fluid inflow and outflow sources to contemporaneously (i) control pressure within the uterine cavity by modulating the positive and negative pressure sources and (ii) control operating parameters of the electrosurgical resecting device. The controller 315 can be adapted to selectively control flows to the uterine cavity through a flow channel at any rate between 0 ml/min and 750 ml/min. In another aspect of the invention, the controller 315 can be adapted to selectively control pressure in the uterine cavity at any level between 0 mmHg and 150 mmHg. The controller 315 can be adapted to selectively control outflows from the uterine cavity through a channel in the system at any rate between 0 ml/min and 750 ml/min. In one variation, the pressure sensor 335 (FIG. 15) is disposable and is detachably coupled to a proximal end of a channel that has a cross-sectional area of greater than $0.1 \text{ mm}^2$, greater than $0.5 \text{ mm}^2$ or greater than $1.0 \text{ mm}^2$.

Figure 17:
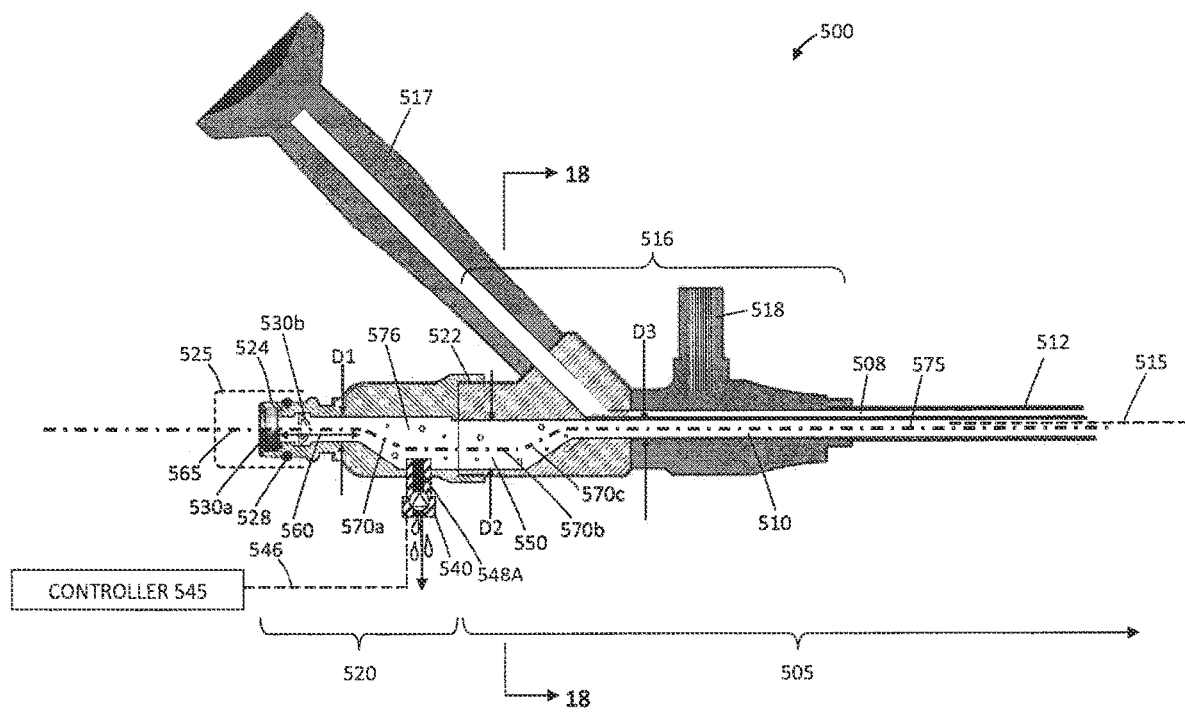
FIG. 17 is a sectional view of a handle portion of an endoscope having an expanded cross-section channel that provides a fluid reservoir and a solenoid-relief valve mechanism for rapid release of fluid from the system to reduce uterine cavity pressure.
Figure 18:
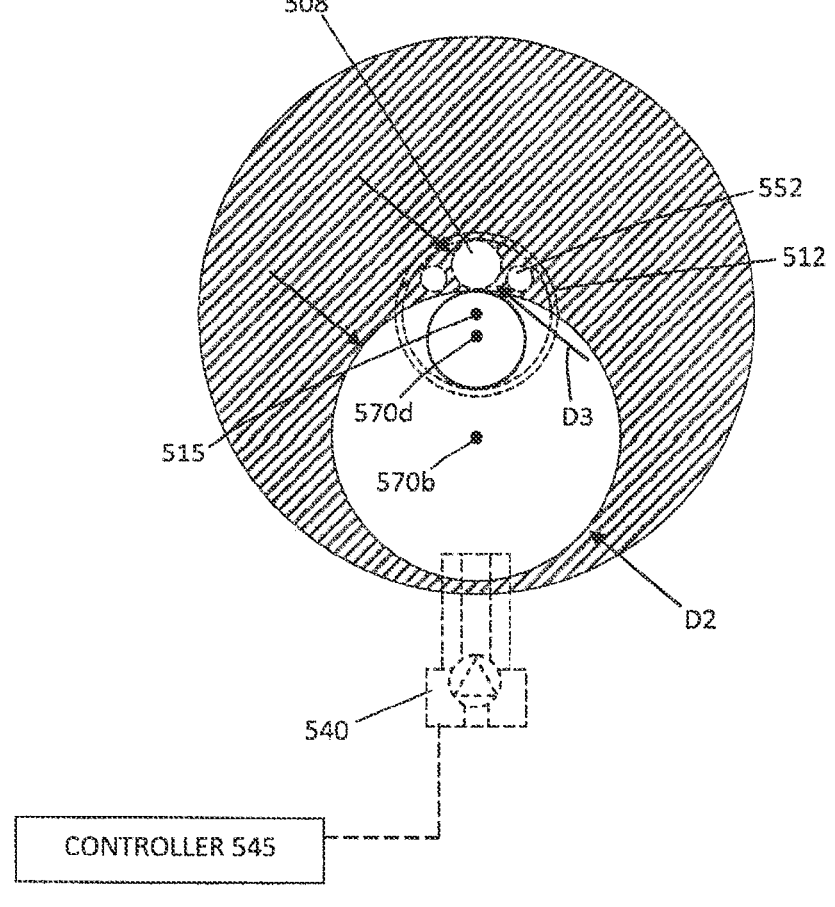
FIG. 18 is a cross-section of the handle portion of FIG. 17 taken along line 18-18 of FIG. 17.

FIGS. 17 and 18 illustrate another variation of endoscope 500 that is configured for use in hysteroscopy that includes mechanisms and systems for controlling pressure in a uterine cavity during a fibroid removal procedure. In one variation, the endoscope 500 and system is adapted to automatically reduce intracavity pressure within a predetermined time interval after a set point of intracavity pressure has been reached. The predetermined set point can be 50 mm Hg, 60 mm Hg, 70 mm Hg, 80 mm Hg, 90 mm Hg, 100 mm Hg, 110 mm Hg, 120 mm Hg, 130 mm Hg, 140 mm Hg, 150 mm Hg, 160 mm Hg, 170 mm Hg or 180 mm Hg. In one variation, the predetermined pressure is 150 mm Hg. The predetermined interval can be in a range between 1 second and 10 seconds and in one variation is 5 seconds. In another variation, the system includes a pressure relief valve for releasing pressure at a predetermined maximum pressure which can in the range of 150 mm Hg to 200 mm Hg and in one variation is 200 mm Hg. Of particular interest, the system is adapted to respond to a measurement of "actual" intracavity pressure measured by a pressure sensor in direct fluidic communication with the uterine cavity. In prior the art, fluid management systems that are adapted to release intracavity pressure at a predetermined set point use only an "estimated" intracavity pressure that is estimated by a software algorithm based on signals relating to fluid inflows communicated to a flow controller. Such prior art systems and algorithms are not capable of accurately measuring "actual" intracavity pressure.

In FIGS. 17-18, it can be seen that endoscope 500 has standard features including a viewing channel 508, a light channel comprising optic fibers in shaft portion 512, a working channel 510 and one or more fluid inflow or outflow channels. The shaft portion 512 of the endoscope extends about central longitudinal axis 515. The endoscope body is reusable and sterilizable as in known in the art. A handle or main body portion 516 of the endoscope body couples to the shaft 512 and carries an eyepiece 517 and luer connectors (not shown) communicating with first and second channels for fluid inflows and outflows as described previously. A light connector is indicated at 518.

As further can be seen in FIG. 17, a proximal endoscope or adapter component 520 comprises a disposable adapter body which is attachable to the proximal end of the endoscope main body. The adapter component 520 can attached by either threads, J-lock or a snap fitting at interface 522 in a configuration that rotationally aligns the channel or lumen portion in component 520 with the channel in the endoscope main body 505.

In one aspect of the invention, the proximal end 524 of the adapter component 520 is configured as a mating portion of a quick-connect fitting 525. The quick-connect fitting 525 and O-ring 528 can be used to couple an outflow tubing 530 directly to the proximal end of the endoscope assembly 500 to allow the system to be used in a diagnostic mode. A diagnostic mode consists of the physician performing a diagnostic procedure before using a resecting probe. Thus, when a resecting probe is not inserted through the endoscope the physician can connect the saline return flow tubing directly to the quick-connect fitting 525 and circulates distention fluid through an inflow channel in the endoscope device and outward through the working channel and outflow tubing coupled to the quick-connect 525 to distend the uterine cavity to thereby allow viewing of the cavity.

The adapter component 520 further carries seals 530a and 530b which comprise seals for (i) preventing fluid outflows through the working channel and adapter when there is no resecting tool disposed the endoscope and for (ii) providing a seal around a resection tool shaft when such a tool is disposed in the endoscope. These seals 530a and 530b can be integrated into a one component or be spaced apart as shown in one variation in FIG. 17.

In one aspect of the invention, as described above, the endoscope assembly includes a valve system configured to automatically reduce uterine cavity pressure within a predetermined time interval after a set point of intracavity pressure has been reached. In one variation, as stated above, the predetermined pressure is 150 mm Hg and the predetermined interval is 5 seconds. In one variation, a solenoid relief valve 540 is operatively coupled to a controller 545 and is adapted to release at least a predetermined volume of distention fluid from the system (endoscope assembly) within a predetermined time interval to insure a very rapid release of pressure in the uterine cavity. In one variation, the predetermined volume is at least 0.1 cc, 0.5 cc, 1 cc, 2 cc, 3 cc, 5 cc or 10 cc within 1 second to release intracavity pressure. The controller 545 receives pressure signals from a pressure sensor coupled directly to an outflow channel in the endoscope as described previously. The controller 545 also can be configured to close the relief valve 540 after a predetermined time interval during which intracavity pressure is below the set point, which interval can be at least 1 second, 2 seconds, 5 seconds or 10 seconds.

In one variation shown schematically in FIG. 17, the adapter component 520 is configured to carry the solenoid or relief valve 540 which is coupled to a system controller 545 through cable 546. The solenoid relief valve 540 also can include an integrated pressure sensor 548A coupled to the system controller 545 through cable 546 wherein a pressure signal at the predetermined pressure will then actuate the solenoid valve 540 to release fluid from the interior channel to the environment to lower intracavity pressure. The pressure sensor 548A communicates with the uterine cavity through fluid in the working channel 510 (around a tool in channel 510) to directly sense pressure in the uterine cavity.

Figure 19:
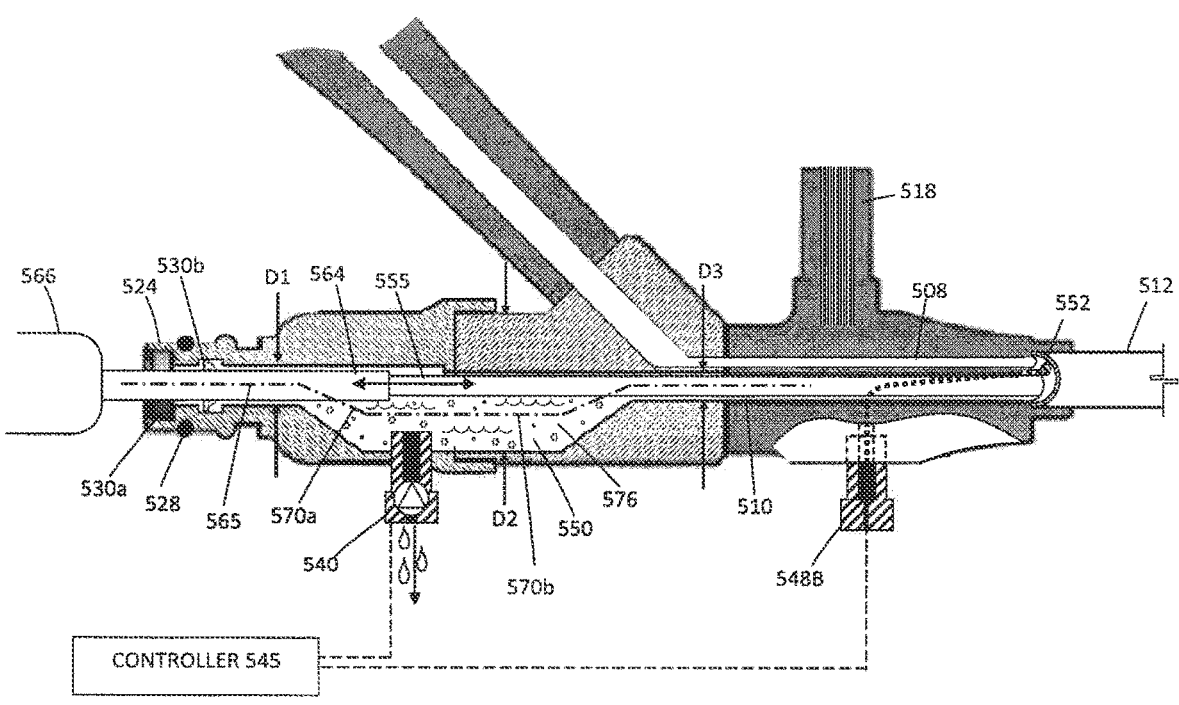
FIG. 19 is a sectional view of a handle portion of another endoscope similar to that of FIG. 17.

In another variation shown in FIG. 19, an independent pressure sensor 548B is shown that communicates with an independent flow channel 552 in the endoscope shaft 512 to allow direct measurement of uterine cavity pressure. The pressure sensor 548B again is operatively connected to controller 545.

In another variation, a signal of a selected level of high pressure from a pressure sensor can terminate RF energy delivery or reciprocation/rotation of a resecting device. In another variation, a signal of a selected level of high pressure from a pressure sensor can trigger a change in inflows or outflows caused by a pump component of the fluid management system.

In FIGS. 17 and 18, if can be seen that the interior of the adapter 520 and interior of endoscope main body portion 516 are configured with a mating open space or expanded offset-axis channel portion 550 that enables optimal functioning of the solenoid relief valve 540. As can be seen in FIG. 19, a probe or tool shaft 555 of a resecting device is shown after having been introduced through the endoscope 500 and the shaft 555 has a dimension that occupies a substantial cross-section of the tool-receiving working channel 510. In the variation of FIGS. 17 and 19, the tool shaft 550 is introduced, in order, (i) through proximal end 524 of the adapter 520 and through channel 560 having longitudinal axis 565 in the proximal portion of the adaptor that has length AA, (ii) through interior expanded offset-axis channel portion 550 in the adapter 520 and proximal portion of handle 516 that has diameter D2, and (iii) through distal channel 510 (diameter D3) of the endoscope shaft portion 512. As can be seen in FIGS. 17-18, the diameter D1 of channel 560 is dimensioned to accommodate a stiffener sleeve 564 that extends around a proximal portion of probe shaft 555 adjacent the handle 566 of the resecting probe 100 (see FIG. 1). Referring to FIG. 17, it can be seen that channel 560 extends along axis 515 and the offset-axis channel portion 550 extends along a central axes 570a, 570b and 570c, and the distal channel 510 extends along axis 575.

FIG. 19 depicts tool shaft 555 disposed within the endoscope assembly and it can be seen that the volume of the offset-axis channel portion 550 enables optimal functioning of the solenoid relief valve 540 since the valve interfaces with a substantial volume of a fluid column that extends to the uterine cavity. As can be seen schematically in FIGS. 20A and 20, the relief valve 540 interfaces with a large volume of fluid 576 in expanded offset-axis channel 550 which communicates with the uterine cavity through a smaller volume of fluid in the annular space 577 around shaft 555 in elongated distal channel 510 that extends through the assembly. As can be easily understood, the release of fluid from channel portion 550 responds to the pressure differential between interior channel portion 550 and the external environment, which upon opening the relief valve 540, can result in very rapid release of fluid as described above. In one variation, the volume of expanded offset-axis channel 550 is at least 1 cc, 5 cc or 10 and the fluid release rate can be at least 0.1 cc, 0.5 cc, 1 cc, 2 cc, 3 cc, 5 cc or 10 cc within 1 second to release pressure in the uterine cavity. Thereafter, the pressure differential between the channel portion 550 and the uterine cavity will result an instantaneous reduction in pressure in the uterine cavity.

Figure 20A:
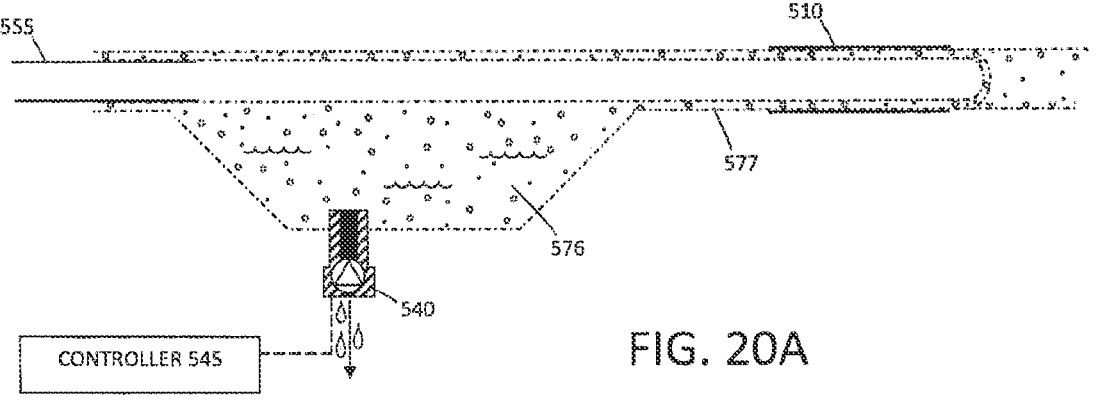
FIG. 20A is a schematic view of an annular flow channel and fluid reservoir in the endoscope handle portion of FIGS. 17-19.
Figure 20B:
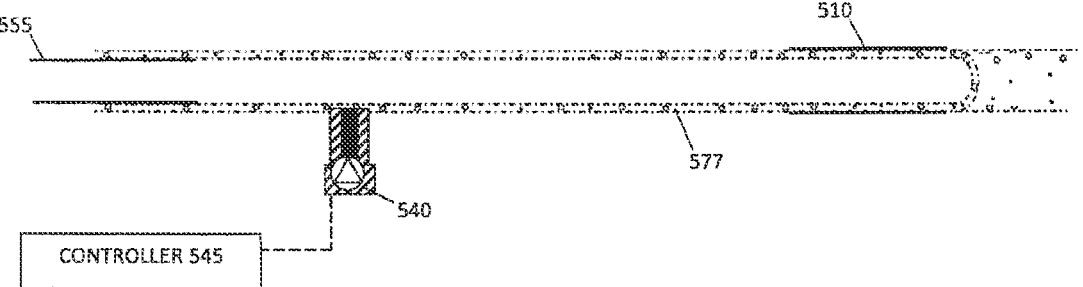
FIG. 20B is a schematic view of an annular flow channel in an endoscope handle portion without the fluid reservoir as in the variation of FIGS. 17-19.

In another aspect of the invention, referring to FIGS. 20A-20B, the fluid volume 576 in the expanded offset-axis channel 550 is needed to prevent transient pressure spikes on pressure sensor 548A which can be introduced by axial movement of probe shaft 555 in the assembly. It can be easily understood that if the tool shaft 555 is moved axially in the variation of FIG. 20B, there could be transient effects on any pressure sensor having fluid contact with the small annular space 577.

In another aspect of the invention, the small annular space 577 can be transiently impinged on by flexing the assembly during use or by mucous, blood, and/or tissue debris clogging the annular space 577. Thus, the fluid volume 576 in the expanded offset-axis channel 550 thus provides, in effect, a fluid reservoir in which mucous, tissue debris, etc. can settle or circulate and reduce the chance of debris impinging on the flow path through the relief valve 540. If a pressure sensor is positioned in channel 550, the fluid volume 576 in offset-axis channel 550 further functions as a buffering reservoir against transient changes in the cross-section of annular space 577 due to flexing of the device. It can be understood from FIG. 20B that a sensor 540' in an annular space 577' (without a buffering reservoir volume 576 of FIG. 20A) can lead to a clogged sensor interface or fluctuations in pressure signals which would detract from system operation.

Figure 21:
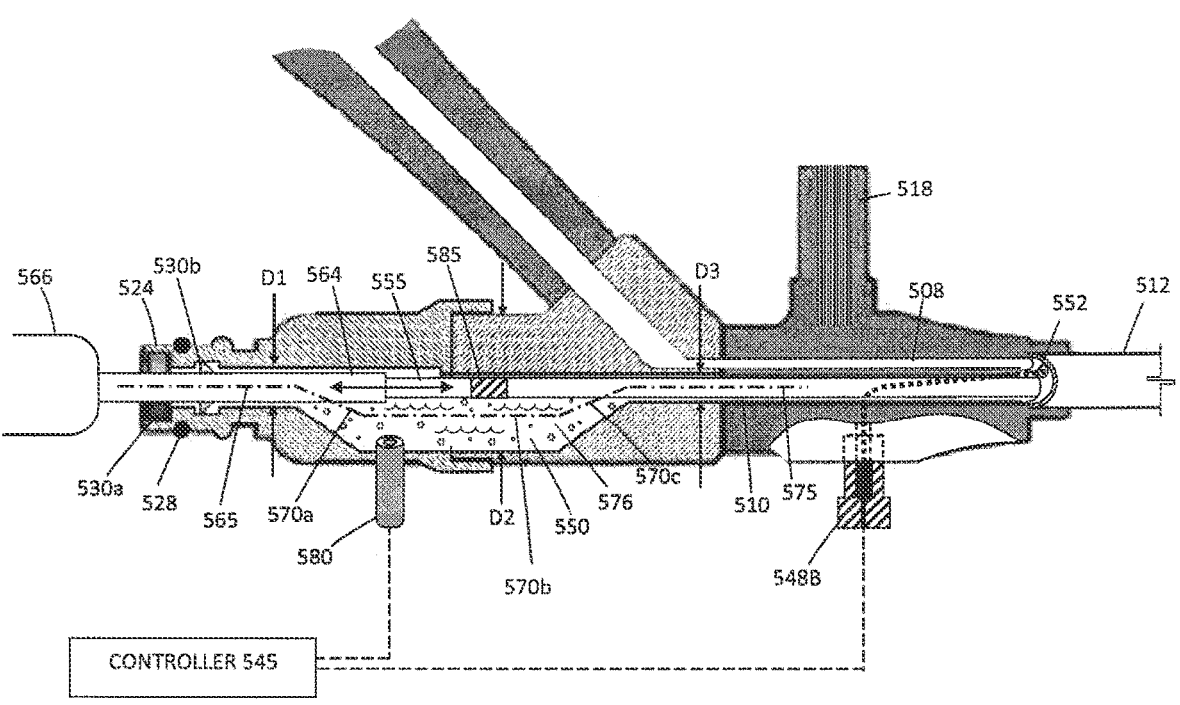
FIG. 21 is a sectional view of a handle portion of another endoscope similar to that of FIGS. 17-18 with an optical sensor.

Referring to FIG. 21, another embodiment has an optical sensor 580 in expanded offset-axis channel 550 that cooperates with a marking 585 on the probe shaft 555 to determine the axial location of the shaft 555 relative to the sensor. In one variation, the position sensing system is operatively coupled to controller 545 to terminate RF delivery to the probe in the event the physician withdrew the probe working end into the working channel 510 with RF energy still activated. Contacting the plasma resecting edge with the endoscope could damage the endoscope.

Figure 22:
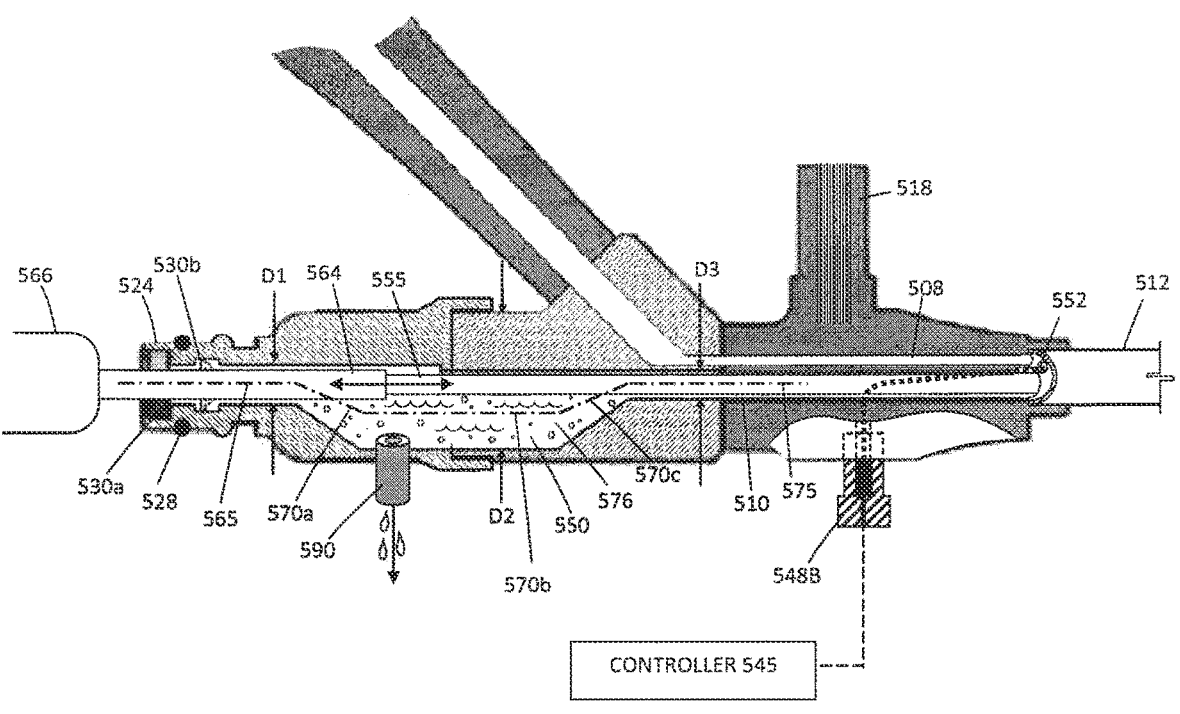
FIG. 22 is a sectional view of a handle portion of another endoscope similar to that of FIGS. 17-18 with a passive pressure relief valve.

In another variation, referring to FIG. 22, a passive pressure relief valve 590 can be disposed in the component 520 to release pressure at a predetermined pressure, for example, at least 150 mm Hg, 160 mm Hg, 170 mm Hg, 180 mm Hg, 190 mm Hg or 200 mm Hg. This passive relief valve can be used in combination with the controller operated solenoid.

In another variation, a temperature sensor can be disposed in the component 520 to measure temperature of the fluid in channel 550 as an additional safety mechanism. It should be appreciated that a pressure sensor can be provided in any embodiment of FIGS. 17-22 in communication with the expanded off-axis chamber 550, in the location of the pressure relief valve shown in FIGS. 17-22.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. An endoscopic system, comprising:
an endoscope having a main body portion and a shaft portion extending distally from the main body portion, the endoscope including a working channel, an optics channel, and at least one fluid flow channel; and
a tissue resecting device including an elongate outer sleeve configured for introduction through the working channel of the endoscope;
wherein the working channel extends from a distal end of the shaft portion through the shaft portion and the main body portion to a port at a proximal face of the main body portion, the working channel including a non-straight portion disposed within the main body portion and a straight channel portion extending longitudinally through the shaft portion to the distal end, wherein the non-straight portion is configured to limit axial sliding of the tissue resecting device within the working channel;
wherein the optics channel extends from a distal end of the shaft portion through the shaft portion and the main body portion to an optics connector on an exterior of the main body portion;
wherein the at least one fluid flow channel extends from a distal end of the shaft portion through the shaft portion and the main body portion to a connector on an exterior of the main body portion.

2. The endoscopic system of claim 1, further including a disposable adapter component coupleable to a proximal end of the main body portion.

3. The endoscopic system of claim 2, wherein a lumen through the disposable adapter component is configured to communicate with the working channel when the disposable adapter component is coupled to the main body portion.

4. The endoscopic system of claim 3, wherein the disposable adapter component includes at least one seal configured to seal around the outer sleeve when the outer sleeve of the tissue resecting device is disposed within the working channel through the lumen of the disposable adapter component, and the at least one seal is configured to seal the lumen when the outer sleeve of the tissue resecting device is absent from the working channel.

5. The endoscopic system of claim 2, wherein the endoscope is free of structure protruding into the working channel between the proximal face of the main body portion and the distal end of the shaft portion.

6. The endoscopic system of claim 1, wherein the non-straight portion of the working channel has a curved centerline.

7. The endoscopic system of claim 1, wherein the non-straight portion of the working channel acts as a resistance feature to limit axial sliding of the outer sleeve within the working channel.

8. The endoscopic system of claim 1, wherein the straight channel portion includes a central longitudinal axis extendable to the proximal face to define a hypothetical central axis, wherein a central axis of the non-straight portion at the proximal face is offset from the hypothetical central axis of the straight channel portion at the proximal face.

9. An endoscopic system for working within a body cavity, comprising:
an endoscope having a main body and an elongate shaft extending distally from the main body, the endoscope including a working channel extending through the main body and the elongate shaft, an optics channel extending from the main body through the elongate shaft, and at least one fluid flow channel extending from the main body through the elongate shaft; and a tissue resecting device including an elongate outer sleeve configured for introduction through the working channel of the endoscope;

wherein the main body includes an angled extension portion having optics communicating with the optics channel;

wherein the working channel has a straight channel portion extending longitudinally through the elongate shaft to a distal end of the elongate shaft, the working channel extends proximally to an aperture in a proximal face of the main body, and a center of the aperture is offset from an axis of the straight channel portion extended to the proximal face, wherein a portion of the working channel within the main body is configured to limit axial sliding of the tissue resecting device within the working channel.

10. The endoscopic system of claim 9, further comprising a video camera coupled to a proximal end of the angled extension portion.

11. The endoscopic system of claim 9, further comprising a light source coupled to the main body of the endoscope.

12. The endoscopic system of claim 9, further comprising a pressure sensor coupled to the main body to measure pressure within the body cavity.

13. The endoscopic system of claim 12, wherein the endoscope includes first and second fluid flow channels extending distally through the elongate shaft from the main body.

14. The endoscopic system of claim 13, wherein the pressure sensor is coupled to the first fluid flow channel.

15. The endoscopic system of claim 9, wherein the center of the aperture is offset from an axis of the straight channel portion extended to the proximal face by about 2 mm to 5 mm.

16. An endoscopic system for working within a body cavity, comprising:

an endoscope having a main body coupled to an elongate shaft extending distally therefrom;

first, second, and third channels extending from the main body to a distal end of the elongate shaft;

a proximal end of the first channel coupleable to a fluid source to provide fluid flow through the first channel;

a proximal end of the second channel coupleable to a pressure sensor for determining a fluid pressure within the body cavity; and a tissue resecting probe configured for introduction through the third channel, wherein the third channel has a straight channel portion that extends longitudinally through the elongate shaft and a proximal channel portion that extends through the main body;

wherein a central axis of the proximal channel portion of the third channel at a proximal face of the main body is offset from a hypothetical central axis of the straight channel portion of the third channel if extended to the proximal face of the main body;

wherein the main body includes an angled extension portion with optics at a proximal end of the angled extension portion, the optics allowing viewing through an optics channel;

wherein the proximal channel portion is configured to provide a selected level of resistance to axial sliding of the tissue resecting probe through the third channel while permitting rotation of the probe within the third channel.

17. The endoscopic system of claim 16, wherein a video camera is couplable to the optics at the proximal end of the angled extension portion.

18. The endoscopic system of claim 16, wherein the tissue resecting probe includes an elongate shaft assembly comprising an outer sleeve with a lumen therein and an inner sleeve that can reciprocate in the lumen.

19. The endoscopic system of claim 16, wherein the central axis of the proximal channel portion of the third channel at the proximal face of the main body is offset from the hypothetical central axis of the straight channel portion of the third channel if extended to the proximal face of the main body by about 2 mm to 5 mm.

20. The endoscopic system of claim 16, further including a disposable adapter component coupleable to a proximal end of the main body such that a lumen through the disposable adapter component is configured to communicate with the third channel when the disposable adapter component is coupled to the main body.

* * * * *